United States Patent
Koob et al.

(10) Patent No.: US 9,393,105 B2
(45) Date of Patent: *Jul. 19, 2016

(54) IN VIVO HYDRAULIC FIXATION INCLUDING BIO-RIVETS USING BIOCOMPATIBLE EXPANDABLE FIBERS

(71) Applicant: Shriners Hospitals for Children, Tampa, FL (US)

(72) Inventors: Thomas J. Koob, Kennesaw, GA (US); Douglas Pringle, Brandon, FL (US)

(73) Assignee: Shriners Hospitals for Children, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/480,679

(22) Filed: Sep. 9, 2014

(65) Prior Publication Data

US 2014/0379081 A1 Dec. 25, 2014

Related U.S. Application Data

(62) Division of application No. 12/034,004, filed on Feb. 20, 2008, now Pat. No. 8,858,633.

(60) Provisional application No. 60/890,679, filed on Feb. 20, 2007.

(51) Int. Cl.
*A61F 2/08* (2006.01)
*A61L 27/24* (2006.01)
(Continued)

(52) U.S. Cl.
CPC .................. *A61F 2/08* (2013.01); *A61F 2/0811* (2013.01); *A61L 27/24* (2013.01); *A61L 27/50* (2013.01); *A61F 2002/087* (2013.01); *A61F 2002/0817* (2013.01); *A61F 2002/0835* (2013.01); *A61F 2002/0876* (2013.01); *A61F 2002/0882* (2013.01); *A61F 2002/0888* (2013.01); *A61F 2210/0061* (2013.01); *A61F 2250/001* (2013.01); *A61L 2430/10* (2013.01)

(58) Field of Classification Search
CPC ..................................................... A61F 2/0811
See application file for complete search history.

(56) References Cited

U.S. PATENT DOCUMENTS

| | | | |
|---|---|---|---|
| 3,316,699 A | 5/1967 | Mattingly | |
| 4,590,928 A | 5/1986 | Hunt et al. | |
| 4,792,336 A | 12/1988 | Hlavacek et al. | 623/13 |

(Continued)

FOREIGN PATENT DOCUMENTS

| | | |
|---|---|---|
| CA | 2285161 | 4/2001 |
| EP | 1493404 | 1/2005 |

(Continued)

OTHER PUBLICATIONS

Brunelli et al., Slip-knot flexor tendon suture in zone II allowing immediate mobilisation, The Hand, 1983, vol. 15, pp. 352-358.

(Continued)

*Primary Examiner* — Jacqueline Woznicki
(74) *Attorney, Agent, or Firm* — Myers Bigel & Sibley, P.A.

(57) ABSTRACT

The disclosure describes implantable medical products, that include dry or partially hydrated biocompatible constructs comprising collagen fibers configured to expand in situ after implantation to frictionally engage a bone tunnel wall to thereby affix the construct in the bone tunnel.

4 Claims, 15 Drawing Sheets

(51) Int. Cl.
  *A61L 27/50* (2006.01)
  *A61F 2/28* (2006.01)

(56) References Cited

U.S. PATENT DOCUMENTS

| | | | |
|---|---|---|---|
| 4,841,962 A | 6/1989 | Berg et al. | |
| 4,883,486 A | 11/1989 | Kapadia et al. | |
| 4,979,956 A | 12/1990 | Silvestrini | |
| 5,078,744 A | 1/1992 | Chvapil | |
| 5,106,949 A | 4/1992 | Kemp et al. | |
| 5,256,418 A | 10/1993 | Kemp et al. | |
| 5,263,984 A | 11/1993 | Li et al. | |
| 5,378,469 A | 1/1995 | Kemp et al. | |
| 5,656,605 A | 8/1997 | Hansson et al. | |
| 5,713,374 A | 2/1998 | Pachence et al. | 128/898 |
| 5,718,012 A | 2/1998 | Cavallaro | |
| 5,718,717 A | 2/1998 | Bonutti | 606/232 |
| 6,090,117 A | 7/2000 | Shimizu | |
| 6,224,630 B1 | 5/2001 | Bao et al. | 623/17.16 |
| 6,277,397 B1 | 8/2001 | Shimizu | |
| 6,280,474 B1 | 8/2001 | Cassidy et al. | 623/16.11 |
| 6,292,697 B1 | 9/2001 | Roberts | |
| 6,335,007 B1 | 1/2002 | Shimizu et al. | |
| 6,531,147 B2 | 3/2003 | Sawhney et al. | |
| 6,565,960 B2 | 5/2003 | Koob et al. | 428/304.4 |
| 6,589,257 B1 | 7/2003 | Shimizu | |
| 6,592,623 B1 | 7/2003 | Bowlin et al. | |
| 6,645,247 B2 | 11/2003 | Ferree | 623/17.11 |
| 6,692,528 B2 | 2/2004 | Ward et al. | 623/17.12 |
| 6,713,537 B1 | 3/2004 | Ueda et al. | |
| 6,730,124 B2 | 5/2004 | Steiner | 623/13.14 |
| 6,752,831 B2 | 6/2004 | Sybert et al. | |
| 6,821,530 B2 | 11/2004 | Koob et al. | 424/458 |
| 6,936,072 B2 | 8/2005 | Lambrecht et al. | 623/17.16 |
| 6,955,683 B2 | 10/2005 | Bonutti | 606/232 |
| 7,084,082 B1 | 8/2006 | Shimizu | |
| 7,090,690 B2 | 8/2006 | Foerster et al. | 606/232 |
| 7,115,146 B2 | 10/2006 | Boyer et al. | 623/23.63 |
| 7,135,040 B2 | 11/2006 | Wang et al. | |
| 7,309,359 B2 | 12/2007 | Trieu et al. | 623/17.16 |
| 7,354,627 B2 | 4/2008 | Pedrozo et al. | |
| 2001/0018619 A1 | 8/2001 | Enzerink et al. | |
| 2002/0037940 A1 | 3/2002 | Koob et al. | |
| 2002/0123805 A1 | 9/2002 | Murray et al. | |
| 2003/0100108 A1 | 5/2003 | Altman et al. | |
| 2003/0230316 A1 | 12/2003 | Glucksman et al. | |
| 2004/0110439 A1 | 6/2004 | Chaikof et al. | |
| 2004/0131562 A1 | 7/2004 | Gower et al. | |
| 2004/0193241 A1 | 9/2004 | Stinson | |
| 2004/0224406 A1 | 11/2004 | Altman et al. | |
| 2004/0267362 A1 | 12/2004 | Hwang et al. | |
| 2006/0095134 A1 | 5/2006 | Trieu et al. | 623/17.16 |
| 2006/0257377 A1 | 11/2006 | Atala et al. | |
| 2006/0263417 A1 | 11/2006 | Lelkes et al. | |
| 2007/0118217 A1 | 5/2007 | Brulez et al. | |
| 2007/0248643 A1 | 10/2007 | Devore et al. | |
| 2008/0020012 A1 | 1/2008 | Ju et al. | |
| 2008/0038352 A1 | 2/2008 | Simpson et al. | |
| 2008/0124371 A1 | 5/2008 | Turos et al. | |
| 2008/0161917 A1 | 7/2008 | Koob et al. | |
| 2008/0188933 A1 | 8/2008 | Koob et al. | |
| 2008/0215150 A1 | 9/2008 | Koob et al. | |
| 2009/0216233 A1 | 8/2009 | Wiedrich et al. | |
| 2009/0287308 A1 | 11/2009 | Davis et al. | |

FOREIGN PATENT DOCUMENTS

| | | |
|---|---|---|
| WO | WO 96/14095 | 5/1996 |
| WO | WO 01/72241 | 10/2001 |
| WO | WO 2008/041183 | 8/2008 |

OTHER PUBLICATIONS

Greis et al, The influence of tendon length and fit on the strength of the tendon-bone tunnel complex, Am. J. Sports Med., 2001, 29:493-497.
Becker et al., Early active motion following a beveled technique of flexor tendon repair: Report on fifty cases, Journal of Hand Surgery, 1979, vol. 4 No. 5, pp. 454-460.
Koob et al., Biomimetic approaches to tendon repair, Comp. Biochem. Physiol. A Mol. Integr. Phys., 2002, 133: 1171-1192.
Koob at al., Material properties of NDGA-collagen composite fibers: development of biologically based tendon constructs, Biomaterials, 2002, 23:202-212.
Koob et al., Mechanical and thermal properties of novel polymerized NDGA-gelatin hydrogels, Biomaterials, 2002, 24:1285-1292.
Messina, The double armed suture: Tendon repair with immediate mobilization of the fingers, Journal of Hand Surgery, 1992, 17A:137-142.
Powell et al., Forces transmitted along human flexor tendons during passive and active movements of the fingers, J. Hand Surg., 2004, 29:4:386-389.
Rodeo et al., Tendon healing in a bone tunnel. A biomechanical and histological study in a dog, J. Bone Joint Surg., 1993, 75:1795-1803.
Savage et al., Flexor tendon repair using a "six strand" method of repair and early active mobilisation, Journal of Hand Surgery, (British vol. 1989), 14B:396-399.
Silva et al., The insertion site of the canine flexor digitorum profundus tendon heals slowly following injury and suture repair, J. Orthop. Res., 2002, 20:447-453.
Trotter et al., Molecular structure and functional morphology of echinoderm collagen fibrils, Cell Tiss., Res., 1994, 275: 451-458.
International Search Report and Written Opinion for corresponding PCT No. PCT/US2008/002230, date of mailing Jul. 16, 2009.
Grog, The Reef (Square) Knot, Animated Knots by Grog, downloaded at http://www.animatedknots,com/reef/index,php, on May 28, 2009 using WayBack Machine on www.archive.org for publication date of Dec. 26, 2005.
Koob et al., Biocompatibility of NDGA-polymerized collagen fibers, I. Evaluation of cytotoxicity with tendon fibroblasts in vitro, © 2001John Wiley & Sons, Inc.
Koob et al., Biocompatibility of NDGA-polymerized collagen fibers. II, Attachment, proliferation, and migration of tendon fibroblasts in vitro, © 2001John Wiley & Sons, Inc.
Martin et al., Anterior Cruciate Ligament Graft Preparation: A New and Quick Alternative to the Whipstitch, Arthroscopy: The Journal of Arthroscopic & Related Surgery, Online Publication Date of Nov. 29, 2006.
Nottage et al., Arthoscopic Knot Tying Techniques, Arthroscopy: The Journal of Arthroscopic & Related Surgery 15(1999): 515-521.
Product advertisement, Conair QB3ECS Quick Braid Styling Kit, © 2007 (1 page).
Integra™ NeuraGen™ Nerve Guide Product Broacher, 4 pages 2005.
Integra™ NeuraGen™ Nerve Guide, Product Webpage, http://www.integra-ls.com/products/?product=88, Date unknown but believed to be prior to the filed of the present application, 2 pages.
Integra™ NeuraWrap™ Nerve Protector, Product Webpage, http://www.integra-ls.com/products/?product=198, Date unknown but believed to be prior to the filed of the present application, 2 pages.

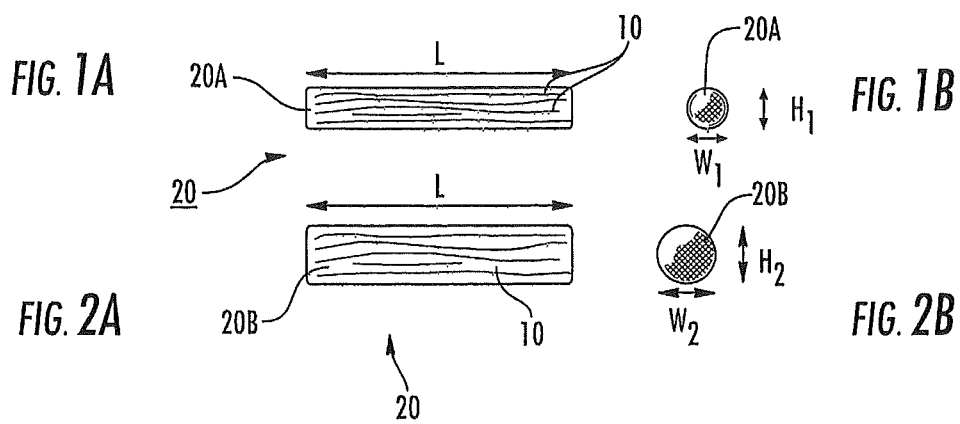
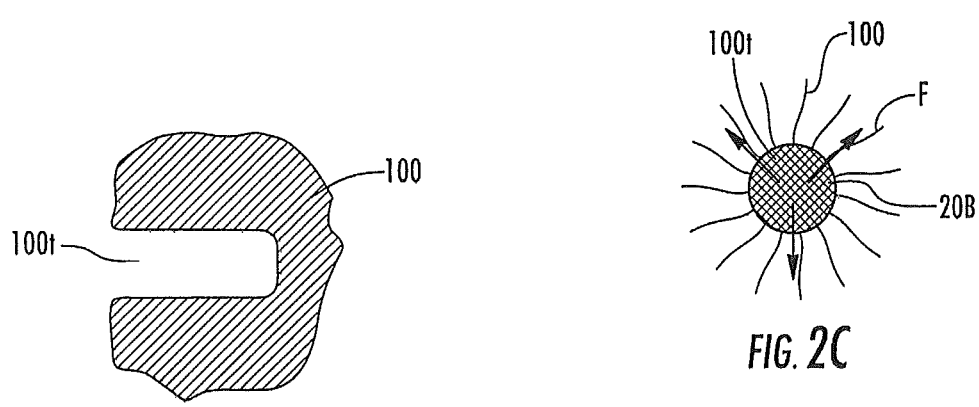
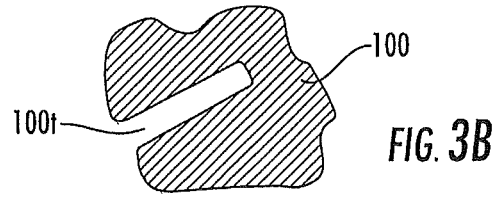
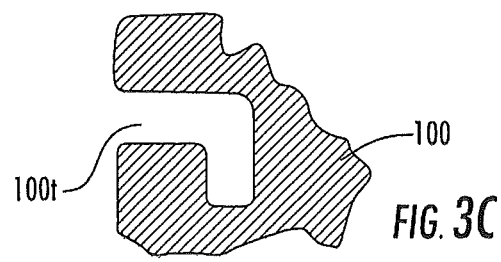

IN VIVO HYDRAULIC FIXATION INCLUDING BIO-RIVETS USING BIOCOMPATIBLE EXPANDABLE FIBERS

RELATED APPLICATION

This application is a divisional of U.S. application Ser. No. 12/034,004, filed Feb. 20, 2008, which claims the benefit of and priority to U.S. Provisional Application Ser. No. 60/890,679, filed Feb. 20, 2007, the contents of each of which are hereby incorporated by reference as if recited in full herein.

FIELD OF THE INVENTION

The invention relates to implantable constructs.

BACKGROUND OF THE INVENTION

The use of an implanted internal prosthetic device to repair dysfunctional tissues in the skeletal system poses complex biomechanical challenges. One challenge is achieving a mechanically competent fixation of the device to the biological tissue at the reconstruction site. Fixation strength should be adequate to withstand loads encountered in vivo during the immediate post-operative period as well as during long-term progressive rehabilitation. Post-operative loads are generally managed by immobilization protocols in order to allow fixation strength to develop coordinately with the repair process. Rehabilitative loads are typically applied once the repaired structure attains sufficient mechanical competence. An effective fixation strategy should be able to achieve immediate fixation during the surgical procedure to maintain the proper positioning of the device during the repair phase and should be able to promote effective integration into the repairing tissue with sufficient fixation strength and functional longevity to allow for tissue ingrowth, such as, for example, neo-tendon or neo-ligament growth.

Current methods for attachment of a graft or bioprosthesis to bone involve drilling, insertion and fixation with adhesives or mechanical fasteners such as interference screws, anchors or buttons. Surgical repair of avulsed tendons and ruptured ligaments often requires joining fibrous biomaterials to bone. Sutures can be used to join the ends of avulsed tendons to bone, and they are fixed in place with bone anchors or buttons, both of which typically require drilling bone tunnels. Tendon autografts are used for anterior cruciate ligament repair, and these are fixed within bone tunnels with interference screws. These fixation approaches have limitations due to one or more of a variety of factors, including invasiveness, the use of non-biological materials, and a propensity of the device to fail with time that is thought to be associated with micro-motion of the bioprosthesis in the bone insertion site. See, e.g., Silva et al, *The insertion site of the canine flexor digitorum profundus tendon heals slowly following injury and suture repair*. J. Orthop. Res. 20:447-453, 2002; Rodeo et al, *Tendon healing in a bone tunnel. A biomechanical and histological study in a dog*. J. Bone Joint Surg. (AM) 75:1795-1803, 1993; and Greis et al, *The influence of tendon length and fit on the strength of the tendon-bone tunnel complex*, Am. J. Sports Med. 29:493-497, 2001. In addition, fixation of biomaterials for tendon and ligament repair in children presents an additional challenge in that these fixation strategies utilize bone tunnels that may traverse the growth plate, creating potential problems for skeletal growth.

SUMMARY OF EMBODIMENTS OF THE INVENTION

Embodiments of the present invention are directed to providing medical implants that allow for hydraulic fixation in vivo.

Embodiments of the invention can include biologically-based fibrous materials configured for insertion into bone tunnels that can swell to frictionally engage local structure and which may eliminate or reduce the need for supplemental conventional fixation devices.

Some embodiments are directed to implantable medical products that include a dry or partially hydrated biocompatible construct comprising collagen fibers configured to expand in situ after implantation to frictionally engage a bone tunnel wall to thereby affix the construct in the bone tunnel.

The collagen fibers can be arranged in an array of substantially parallel polymerized collagen fibers. The collagen fibers may comprise nordihydroguaiaretic acid (NDGA) polymerized collagen fibers. The dry or partially hydrated construct can have a cross-sectional area that is between about 70-98% of that of the bone tunnel before implantation.

In some embodiments, in a fully hydrated unconstrained state, when measured ex vivo, the construct is configured to increase in cross-sectional area, on average, at least about 100%, typically between about 200-300%. The construct may have a substantially constant length, whether in the dry or partially hydrated configuration or the fully hydrated configuration.

In some embodiments, the array of substantially parallel fibers comprise between about 5-200 elongate fibers compressed together so that adjacent fibers snugly contact each other to define the construct.

Other embodiments are directed to implantable ligament or tendon bioprostheses that include a dry or partially hydrated flexible implantable biocompatible construct having a primary body comprising polymerized collagen fibers having opposing first and second end portions. At least one of the end portions is configured to expand in a direction that is substantially orthogonal to an axial direction of the fibers in vivo to frictionally engage a wall of a bone tunnel while the construct retains a substantially constant unconstrained length in a dry or partially hydrated state and in a fully hydrated state.

Still other embodiments are directed to medical rivets that include an implantable partially hydrated or dry rivet comprising a plurality of elongate biologically compatible fibers configured to expand when exposed to liquid to frictionally engage targeted local structure.

The rivet can be sized and configured to be slidably inserted into two aligned adjacent bone tunnels, then expand to frictionally engage respective walls thereof whereby bones housing the respective bone tunnels are held in alignment. The biologically compatible fibers may include polymerized collagen. The rivet can have a dry or partially hydrated cross-sectional area that is between about 80%-98% of that of a bone tunnel configured to hold the rivet. The rivet can be configured to withstand a pull-out force that is at least about 10 N after 24 hours after implantation.

The rivet can be sized and configured for pediatric fracture repairs to extend through bone tunnels in bone (growth) plates.

Yet other embodiments are directed to medical kits that include: (a) an implantable dry or partially hydrated construct having a hydraulic fixation portion comprising collagen fibers; and (b) a sterile package sealably enclosing the hydraulic fixation member therein.

The kits may include a hemostat having an axially-extending center channel configured and sized to snugly hold a leading edge portion of the dry or partially hydrated construct for insertion into a bone tunnel.

Still other embodiments are directed to methods of making a medical construct. The methods include: (a) arranging a plurality of collagen fibers into a prosthesis; (b) dehydrating the collagen fibers forming the prosthesis to a desired dry or partially hydrated state; and (c) enclosing the dry or partially hydrated prosthesis in a sterile package.

The collagen fibers may be polymerized collagen fibers and may be held in tension during the dehydrating step.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 1A is a top view of a partially hydrated or substantially dry array or bundle of fibers used to form an implantable biocompatible hydraulic fixation construct according to embodiments of the present invention.

FIG. 1B is a cross-sectional view of the construct shown in FIG. 1A.

FIG. 2A is a top view of the construct shown in FIG. 1A illustrated in a fully hydrated configuration.

FIG. 2B is a cross-sectional view of the construct shown in FIG. 2A.

FIG. 2C illustrates the construct shown in FIG. 2B inside a bone tunnel according to embodiments of the invention.

FIGS. 3A-3C are exemplary schematic illustrations of bone tunnels according to embodiments of the present invention.

FIGS. 18A and 18B are for cortical bone at a 0.95 mm and 1.0 mm tunnel diameter, respectively, and FIG. 18C is for cancellous bone at a 0.95 mm bone tunnel diameter.

DETAILED DESCRIPTION

Figures 4A, 4B:
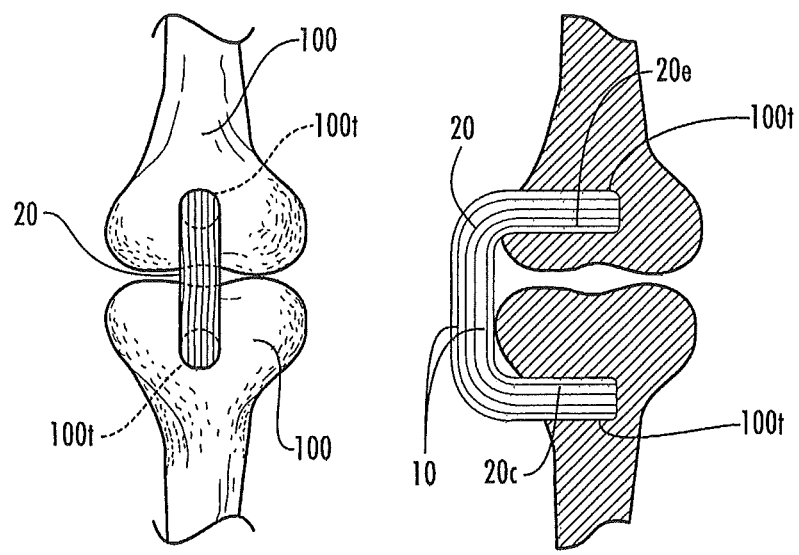
FIG. 4A is a schematic illustration of the construct shown in FIG. 2A in an exemplary use position hydraulically affixed in bone tunnels.
FIG. 4B is a section view of the device in the bone tunnels shown in FIG. 4A according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled to, or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "implant" and "prosthesis" are used interchangeably herein to designate a product configured to repair or replace (at least a portion of) a natural tendon, ligament or other tissue of a mammalian subject (for veterinary or medical (human) applications). The term "implantable" means the device can be inserted, embedded, grafted or otherwise chronically attached or placed on or in a patient. The term "tissue" means skin, muscle, bone or other group of cells.

The term "array" means an arrangement of fibers in rows and/or columns that are held together as in a matrix.

Collagen "microfibrils," "fibrils," "fibers," and "natural fibers" refer to naturally-occurring structures found in a tendon. Microfibrils are about 3.5 to 50 nm in diameter. Fibrils are about 50 nm to 50 µm in diameter. Natural fibers are above 50 µm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber. Of course, synthetic collagen fibers can include non-collagenous components, such as particulates, hydroxyapatite and other mineral phases, or drugs that facilitate tissue growth. For example, the compositions can contain carbon nano-tubes, zinc nano-wires, nano-crystalline diamond, or other nano-scale particulates; larger crystalline and non-crystalline particulates such as calcium phosphate, calcium sulfate, and apatite minerals. For example, the compositions can contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin.

The term "suture" refers to a flexible elongate material that is used to attach the bioprosthesis to a target anatomical structure to help hold the bioprosthesis in location in the body. The suture may be resorbable or non-resorbable, synthetic or natural. The suture can be configured to hold the implant in location for at least an initial post-implantation period of at least about 1 week, but may reside permanently in the body or, as noted above, may be substantially resorbable over time. The suture can be a single filament or multi-filament thread, floss, gut or wire, or combinations thereof that can be used to hold a portion of an implant against or attached to target structures, typically to bone and/or tissue. The suture may comprise a resorbable or non-resorbable biocompatible material. Examples of suture materials include elastomeric materials, such as, for example, polymers, copolymers and/or derivatives thereof, including Vicryl®, as well as other materials including, for example, NITINOL, and combinations thereof. The suture may be used with a suture anchor (bone or tissue anchor), staple, screw, plate or other bio-compatible fixation member to affix the implant in the desired location and/or orientation.

The term "atraumatic" with respect to suture needles with thread refers to an atraumatic or eyeless needle attached to a specific length of suture material (thread or filament). The suture and needle are preformed and purchased as a unit, as the suture needle manufacturer swages or binds the suture thread to the eyeless atraumatic needle at the factory. In a conventional traumatic needle with suture, the thread comes out of the needle's hole or eye on both sides. When passing through the tissues, this type of suture may rip tissue, at least to a certain extent. In contrast to the conventional "trauma"-type needle with suture, the atraumatic needle with suture does not cause trauma (hence the name "atraumatic"). Because of these advantages, atraumatic needles with sutures are today very widely used.

As with conventional sutures, the sutures of atraumatic needles can be absorable or non-absorbable. As is well known, there are several shapes of atraumatic needles, including straight, half curved, one-third curved and others. The body of the needle is available also in different makes, like circular, with edge on the outer side, with edge on the inner side, and others.

The term "flexible" means that the so-called member can be flexed or bent.

The array of fibers can be held together in any suitable manner including by their natural affinity to stick together upon compression or extrusion, by using a sticky coating or adhesive, such as a gelatinous coating, or by otherwise attaching the fibers to form the array. The fibers may also optionally comprise braided segments. The term "braided" and derivatives thereof mean to (inter)weave and/or interlock, in any manner, three or more fibers or bundles of fibers together, including knitting and knotting and combinations of these or other interlocking constructions.

The term "dry" means the construct has a moisture content substantially less than the amount present when fully hydrated. The term "partially hydrated" means that the construct and/or fibers thereof have a moisture content that is less than about 50%, typically less than about 75% of the moisture content at full hydration, measured ex vivo after 24 hours in a saline bath at ambient conditions.

In some embodiments, biocompatible constructs can be placed in bone tunnels or other, typically substantially rigid, target structures. A suitably sized and configured array or bundle of dry or partially hydrated fibers can be inserted into a respective bone tunnel. When exposed to a hydrating environment, the fibers respond by increasing in cross-sectional area and fill and pressurize the bone tunnel, thereby providing an effective frictional restraint. The moisture-induced increase in size to cause the frictional restraint or engagement is referred to as "hydraulic fixation" and a member or construct that provides the hydraulic fixation is a "hydraulic fixation member" or "hydraulic fixation construct".

Generally stated, it is contemplated that hydraulic fixation will be particularly suitable for use in tendon and ligament repairs. Hydraulic fixation constructs can eliminate or reduce the need for peripheral anchoring means such as bone anchors, screws, buttons, sutures, glues or resins or may improve the fixation with such devices. The hydraulic fixation can have an advantage of short insertion and fixation times. Hydraulic fixation may simplify surgery and allow increased, and potentially "normal", joint mobilization within hours after surgery.

The hydraulic fixation technique can be used for any suitable fixation. Non-limiting examples include repair modalities such as, for example, fixation of ligament bioprostheses to bone, fixation of avulsed tendons to bone, and attachment for tendon transfer. The hydraulic fixation member can be packaged in a medical kit as a "fixation" kit. Alternatively, in some embodiments, the hydraulic fixation member can be configured to attach a bioprosthesis alone, or the hydraulic fixation member may cooperate with other attachment members to allow attachment of bioprostheses to allograft bone and/or attachment of bioprostheses to bone anchors. The hydraulic fixation member can be configured to have one or more end portions that hydraulically engage bone. The hydraulic fixation member can be configured to have a flexible primary body portion that can approximate the stiffness and flexibility of tendon and/or ligament. Alternatively, the hydraulic fixation member may be substantially rigid or have increased rigidity in situ (typically with more fibers over the more flexible versions) and function similar to a pin, rivet or other mechanical fixation device.

FIG. 1A is a schematic illustration of an implantable construct 20 with multiple fibers 10 that can be held together to form an array of fibers 10$a$. As shown in FIG. 1A, the multiple fibers 10 can be axially arranged so that at least a majority of the fibers are substantially parallel to each other over at least a major portion of the length of the construct 20, typically over substantially the entire length of the construct 20. Some of the fibers may not run the entire length of the construct 20. The construct 20 shown in FIGS. 1A and 1B is dry or partially hydrated. The construct 20 illustrated in FIGS. 2A and 2B is shown fully hydrated and in a "hydraulic" fixation configuration. As shown in FIG. 1B, the cross-sectional shape of the construct 20 may be substantially round during placement or ex vivo. As shown in FIG. 2B, the shape of the construct 20 can swell to a larger height "$H_2$" and width ("$W_2$") configuration (which may, for a substantially circular, oval or elliptical shape, have an associated diameter "$D_2$"), to take on the shape of the adjacent local structure to frictionally engage therewith, such as, for example, a bone tunnel configuration. That is, as shown in FIG. 2C, if the local structure is a bone tunnel 100$t$ that is formed as a round tunnel, the construct 20 will swell to fill the tunnel and take the corresponding shape as it swells and impart frictional forces against the wall of the bone tunnel to hydraulically affix itself therein. In typical embodiments, the length "L" of the construct is substantially constant between the dry or partially hydrated and hydrated configurations, typically changing less than about 3%.

In some embodiments, the cross-sectional area of the construct 20 is sized to be between about 60%-98% of that of the bone tunnel 100$t$ at insertion, typically between about 75%-90%, to allow for an insertion tool to cooperate with the construct 20 to slide the construct 20 into the tunnel 100$t$ and to allow for sufficient expansion after placement to cause a desired frictional engagement (higher pull-out forces). Measured outside the body, after 24 hours in a saline bath at ambient conditions, the construct 20 can be configured to expand to an increased hydrated unconstrained equilibrium cross-sectional area of between about 50% to about 250%, typically between about 150-220%.

The hydraulic fixation construct 20 may be particularly suitable for ligament and/or tendon repairs, replacements or treatments. The constructs 20 can be configured to have at least about 60% of the tensile strength of natural ligament or tendon at implantation or within about 1-2 days thereof, which strength can increase with neo-tissue in-growth over time, and may have tensile strength and stiffness similar or even greater than the tensile strength, stiffness and/or dynamic flexibility of corresponding natural tissue, e.g., natural ligament or tendon fibers. Thus, embodiments of the invention may be particularly suitable for augmenting, repairing or replacing tendons and ligaments.

The construct 20 can be configured with a substantially planar flexible body for a ligament prosthesis, such as for an ACL repair or replacement. In other embodiments, the construct 20 may be configured as a substantially cylindrical body for a tendon-prosthesis, such as, for example, the flexor tendon. In some embodiments, the construct 20 can have between about 20-75 fibers and be used as a digital flexor tendon. Other configurations may also be used as suitable for the target treatment site/prosthesis.

In some embodiments, the plurality of fibers 10 in a respective construct 20 can be between about five to about two hundred. In some embodiments, the number of fibers 10 forming the construct 20 is between about ten (10) to about fifty (50). For bio-rivet configurations, the number of fibers may be more to add additional structural rigidity, such as between about 100 to about 250, typically between about 100 to about 150. Lesser and greater numbers of fibers may be used depending on the desired tensile strength, rigidity, or other mechanical parameter of the construct at the target implant site.

In some embodiments, the construct 20 is configured to have substantially the same physical thickness and/or configuration as the replaced or repaired tissue so as to not cause discomfort or physical abnormalities in structure when in position.

The array can be a relatively tightly compressed array of fibers or a relatively loosely compressed or attached arrangement having voids between some adjacent fibers depending on the target location and the desired mechanical properties and configuration and to allow for neo-tissue in-growth.

In some embodiments, the construct 20 is between about 0.5-50 cm long, typically between about 1-25 cm, and in some embodiments between about 1 cm to about 10 cm long. The construct 20 may have a width that is between about 0.05 mm to 8 cm, and is typically between about 0.5 mm to about 3 cm. The constructs 20 may have a cross-sectional thickness of about 0.01 to about 30 mm. For the flat construct 20f, the thickness may be more typically between about 0.1 to about 10 mm, while the tubular construct 20r may have a thicker cross-section, such as between about 0.75 mm to about 30 mm.

As shown in FIG. 3A, the bone tunnel(s) 100t that receives the construct 20 may be substantially straight (vertical or horizontal). Alternatively, the tunnel 100t may angle as shown in FIG. 3B depending on the target repair/implant site. In some embodiments, the bone tunnel 100t can include different path trajectories as shown for example in FIG. 3C. The construct 20 can bend to follow the tunnel trajectory during insertion. Having the end portion orthogonal or angled with respect to the other tunnel portion may inhibit pull-out.

The bone tunnel 100t can vary in width (diameter) and length depending on the target application. The length of the bone tunnels 100t is typically between about 3 mm to about 12 mm, with bone tunnels 100t in pediatric bone plates being between about 1 mm to about 4 mm. However, in some particular embodiments the bone tunnel 100t can be configured to have a length that is at least about 5 mm in cortical bone (for adults), and at least about 7 mm in cancellous bone (for adults).

In some embodiments, the biocompatible material 20 is inserted in a dry state and the interstitial fluid environment mediates a hydration process that proceeds until equilibrium is reached. The hydration causes an increase in the cross sectional area of the fibers until they fill the tunnel and cause a build up in internal pressure. The pressure causes a large frictional force, which effectively fixes the prosthesis in the bone tunnel.

The construct 20 and/or fibers 10 can incorporate anti-inflammatory agents or other pharmaceutically suitable agents. The construct 20 and/or fibers 10 can be configured with an anti-swelling inhibitor to control the time or rate of hydration induced-swelling to allow enough time for a clinician to properly orient and adjust the fixation member 20 in situ. For example, the anti-swelling inhibitor may be a heat or light sensitive coating or matrix and/or hydrogel coating or matrix that can dissolve or resorb when in the body over a relatively short period (such as to allow the swelling to occur about 20-60 minutes after placement). In some embodiments, natural body heat may be sufficient to release the coating and initiate the swelling or a clinician may locally apply increased heat. Other swelling-inhibitor removal techniques may be used depending on the inhibitor, such as, for example, applying laser or infrared light, RF heat, heated and/or solvent liquid or fluid irrigation materials, and the like, to release the swelling inhibitor to allow the hydration-induced swelling. The swelling-inhibitor may also be lubricious so as to facilitate slidable insertion as appropriate.

The construct 20 may also or alternatively be coated or impregnated with a thin film of polylactic acid (PLA) or other suitable substance to promote strength and/or ease of handling. For example, the construct 20 can be dipped, painted or sprayed with a 3% solution of PLA in chloroform or other suitable solution.

Figure 5:
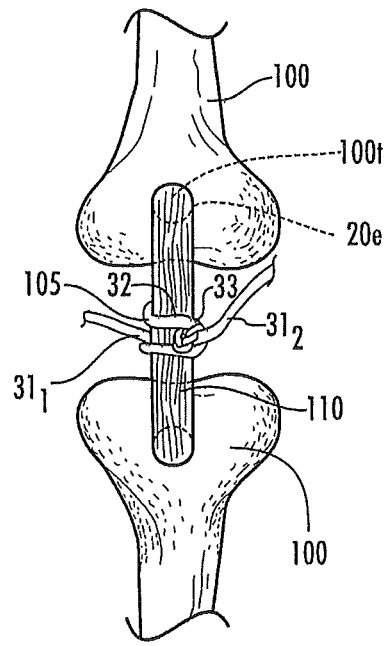
FIG. 5 is a schematic illustration of the construct shown in FIG. 2A with one end portion hydraulically affixed in a bone tunnel and the other end portion affixed to local structure such as tendon, ligament or other muscle or soft tissue.

FIGS. 4A and 4B illustrate the use of the construct 20 for joining opposing end portions 20e of the biologically based fibrous materials to bone tunnels 100t that may reduce or eliminate the need for supplemental mechanical fixation devices or serve as an adjunct fixation strategy. As shown, no additional fixation devices are required. However, surgical adhesives (glue), staples, buttons, sleeves or other devices may be used with the construct 20 depending on the repair site and needs thereof. FIG. 5 illustrates that one end portion of the construct 20e can reside in a bone tunnel 100t while the other end portion is attached to a repair site of a ligament or tendon 110, typically using a suture(s) 105. The integration technique can include drilling at least one bone tunnel 100t to a defined size and inserting an end portion 20e of the construct 20 with a defined size and swelling capacity. As discussed above, at least one end portion 20e of the construct 20 may be configured as a substantially round cross-sectional shape with the elongate body formed by an array of substantially parallel fibers 10. The cross-sectional configuration (shape and/or size) of the array or bundle 20 can be designed to achieve mechanical competence (frictional engagement) for the target application. The size (e.g., width/height or diameter) of the bone tunnel 100t can be designed to provide for a snug fit during initial insertion.

One contemplated use of the construct 20 is a bioprosthesis with one end portion hydraulically engaged in a bone tunnel to bridge gaps in tendon and ligaments by providing the construct 20 in a matching length and suturing into the patient's own remaining tendon or ligament end portions using a suitable surgical tying technique, such as, but not limited to, a double Kessler technique or similar methodology.

FIG. 5 illustrates that a suture 105 can be attached to each end portion of the construct 20e and used to affix the construct 20 to local tendon or ligament. In the embodiment shown in FIG. 5, the suture 105 is tied to the construct 20 so that opposing legs $31_1$, $31_2$ extend from a looped portion 32 of the suture having one or more loops 321 encasing the construct 20 that is tied to form one or more knots 33. The sutures 105 may be resorbable or non-resorbable. Adhesive 22 may be used to help secure one or both of the end portions 20e during an initial healing phase for additional stabilization.

The knot 33 can be configured to provide a secure attachment to the array or fiber bundle 20 and organize the parallel array of fibers into a desired cross-sectional configuration. The knot configuration can position the suture 105 to reach out into adjacent tissue for anchorage at about 180 to about 360 degrees from each other The suture legs $31_1$, $31_2$ can extend substantially parallel to each other from opposing outer lateral edges of the construct 20 in the direction of the target anchoring-site. In the embodiment shown, the sutures 105 are oriented to exit the construct body outside the bounds of the construct itself at opposing side locations and extend substantially parallel to the anchoring site. The looped portion 32 and the knot(s) 33 are configured to improve tensile/compression force distribution and/or cancel unwanted torque. For additional discussion of exemplary knot configurations see, co-pending U.S. Provisional Application Ser. No. 60/890,660, the contents of which are hereby incorporated by reference as if recited in full herein.

Figure 6A:
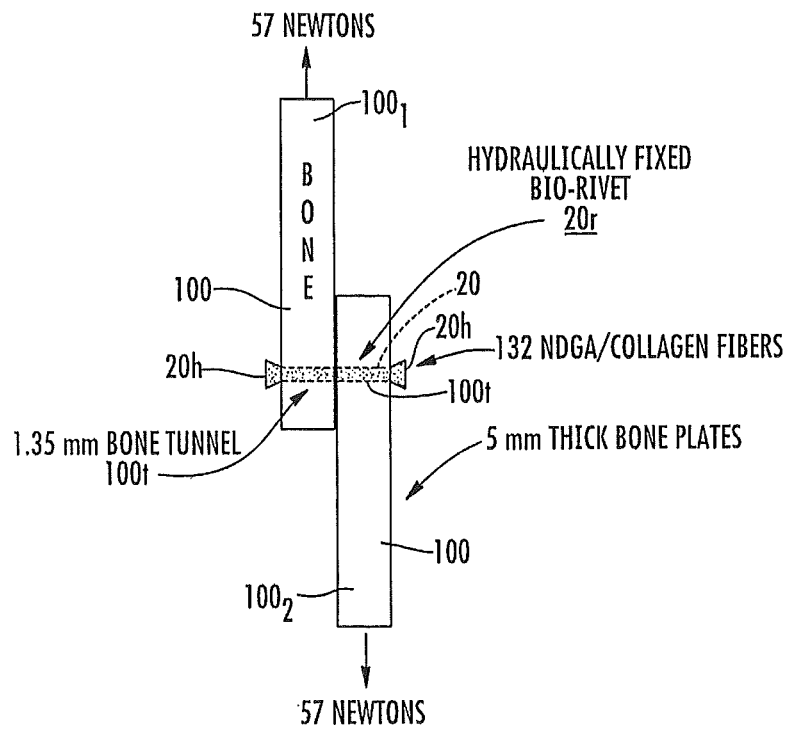
FIG. 6A is a schematic illustration of a hydraulically fixed bio-rivet in an exemplary in vivo position according to embodiments of the invention.

FIG. 6A illustrates the construct 20 can be a hydraulic bio-rivet 20r that, in position, can hold adjacent bones, bone fragments or pieces $100_1$, $100_2$ in a desired alignment. The bones can be bone plates and the bone tunnels 100t may extend all the way through at least one of the bones $100_1$, $100_2$ (as shown, the bio-rivet 20r extends through both bone plates). One or both of the exposed end portions 20e can be configured to define a head 20h. One or both of the heads 20h can be formed after the construct 20 is in position.

In some embodiments, the construct has one head 20h formed prior to insertion into the bone tunnel that extends through both bones. The construct 2Q can bundle the fibers 10 as a single grouping of fibers that form the head 20h when hydrated to cause sufficient swelling to obtain a size that is greater than that of the adjacent tunnel 100t. The head 20h can include a metallic or polymeric substantially rigid member.

Figure 6C:
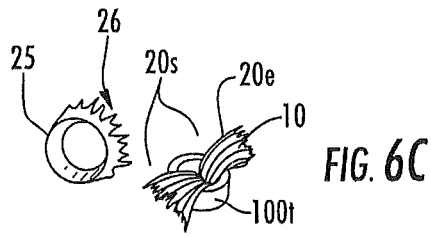
FIG. 6C is an exploded schematic illustration of a holding member that can engage an end portion of a hydraulic fixation member according to embodiments of the present invention.
Figure 6B:
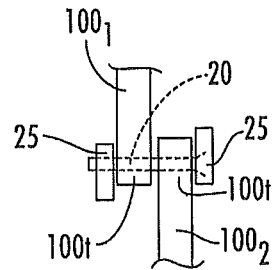
FIG. 6B is a schematic illustration of a hydraulically fixed bio-rivet in an exemplary in vivo position similar to the embodiment shown in FIG. 6A but using mechanical holding members that cooperate with the bio-rivet according to embodiments of the invention.

As shown in FIG. 6B, at least one of the heads 20h (shown as both heads) can be formed by trapping the exiting portion of the fibers 10 in a holding member 25. The holding member 25 can be a resorbable or permanent component, such as, but not limited to, a cap, staple, screw, pin, suture and the like. For example, the exiting portion of the fibers 10 can be captured in a cap 25 and or staple (not shown).

In some embodiments, as shown in FIG. 6C, the construct 20 can be separated into discrete separate fibers 20s or bundles of fibers, which can be formed into the respective head 20h using a mechanical member such as a cap 25. The exiting strands can be braided, folded (FIG. 6D) or otherwise formed and trapped or held against the local bone using a holding member 25.

As shown in FIGS. 6B and 6C, in some embodiments, the holding member comprises a cap 25 or staple (not shown) that can engage the exiting portion of the construct 20e and be used to trap the fibers and define the head 20h. The holding member 25 can be attached to the exiting portion of the fibers 10 in any suitable manner, including being pressed against the fibers 10, adhesively attached thereto, anchored or screwed into the bone, or the like to trap the fibers 10 therebetween.

Figure 6D:
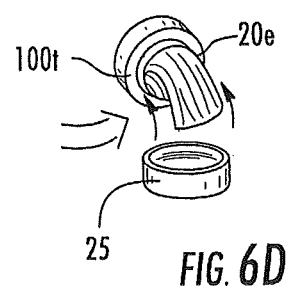
FIG. 6D is an exploded schematic illustration of a holding member that can engage an end portion of a hydraulic fixation member according to other embodiments of the present invention.

FIG. 6C illustrates that the holding member 25 can include a serrated edge 26 that can engage the exposed bone to trap the fibers 10 against the bone to help hold the construct in position. FIG. 6D illustrates the end portion of the construct 20e can be folded over and the holding member 25 used to trap the folded end portion of the construct for additional anchoring stability.

Figure 7:
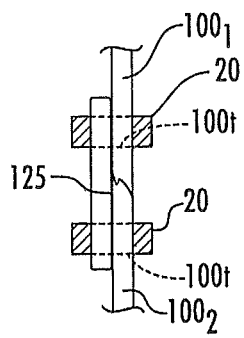
FIG. 7 is a schematic illustration of hydraulic fixation members used to engage a plate and align bone segments according to embodiments of the present invention.
Figure 8:
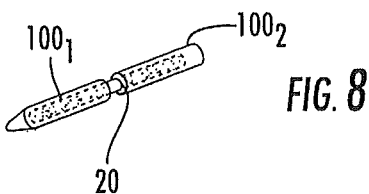
FIG. 8 is a schematic illustration of hydraulic fixation members used as a "pin" substitute to align bone segments according to embodiments of the present invention.

FIG. 7 illustrates that the hydraulic fixation construct 20 can engage a plate 125 to hold bone segments 100 in position. FIG. 8 illustrates that the construct 20 can function as a bio-pin that engages an internal bone tunnel 100t and holds separated portions of bone segments $100_1$, $100_2$ in axial alignment and promote tissue ingrowth. Such a configuration may be particularly suitable for collar-bone fractures, finger fractures, and foot fractures.

Figure 9A:
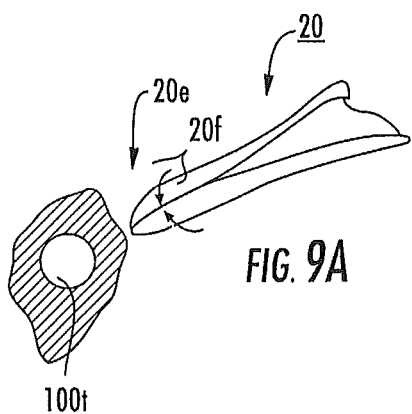
FIG. 9A is an exploded schematic illustration of a construct that can be rolled at one end portion to a desired shape for insertion into a bone tunnel according to embodiments of the present invention.
Figure 9B:
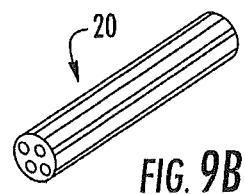
FIG. 9B is a schematic illustration of a substantially cylindrically shaped construct suitable for insertion in the bone tunnel shown in FIG. 9A.
Figure 10:
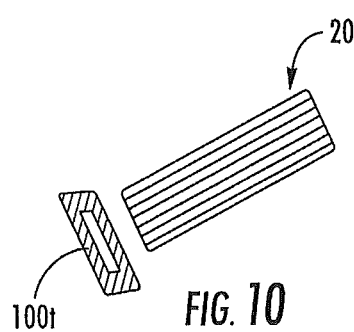
FIG. 10 is an exploded schematic illustration of a substantially flat construct and corresponding bone tunnel according to other embodiments of the present invention.
Figure 11:
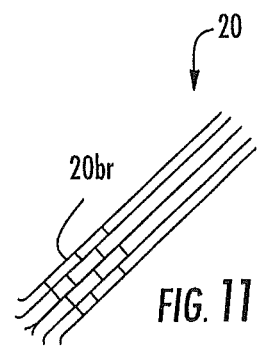
FIG. 11 is a schematic illustration of a construct with a braided segment according to embodiments of the present invention.

FIG. 9A illustrates that at least one end portion 20e of the construct 20 may be rolled, wrapped or folded (see construct 20f in FIG. 9A) for insertion into a substantially round bone tunnel 100t, while FIG. 9B illustrates that the construct 20 can be arranged in a substantially cylindrical shape. FIG. 10 illustrates that the construct may be substantially planar and the bone tunnel configured with a substantially rectangular (or square) shape. FIG. 11 illustrates that the construct may include a braided segment 20br with bundles of fibers braided together. The braided segment 20br may reside at an end portion, a medial portion, or segments therebetween, or may extend substantially the entire length of the construct. Combinations of these shapes may be used. For example, a substantially flat construct 20 can be wrapped about a cylindrical construct body and both (with reduced moisture content) inserted into the target structure. Where two constructs are used, different fiber sizes and numbers may be used to form the constructs.

Figure 12:
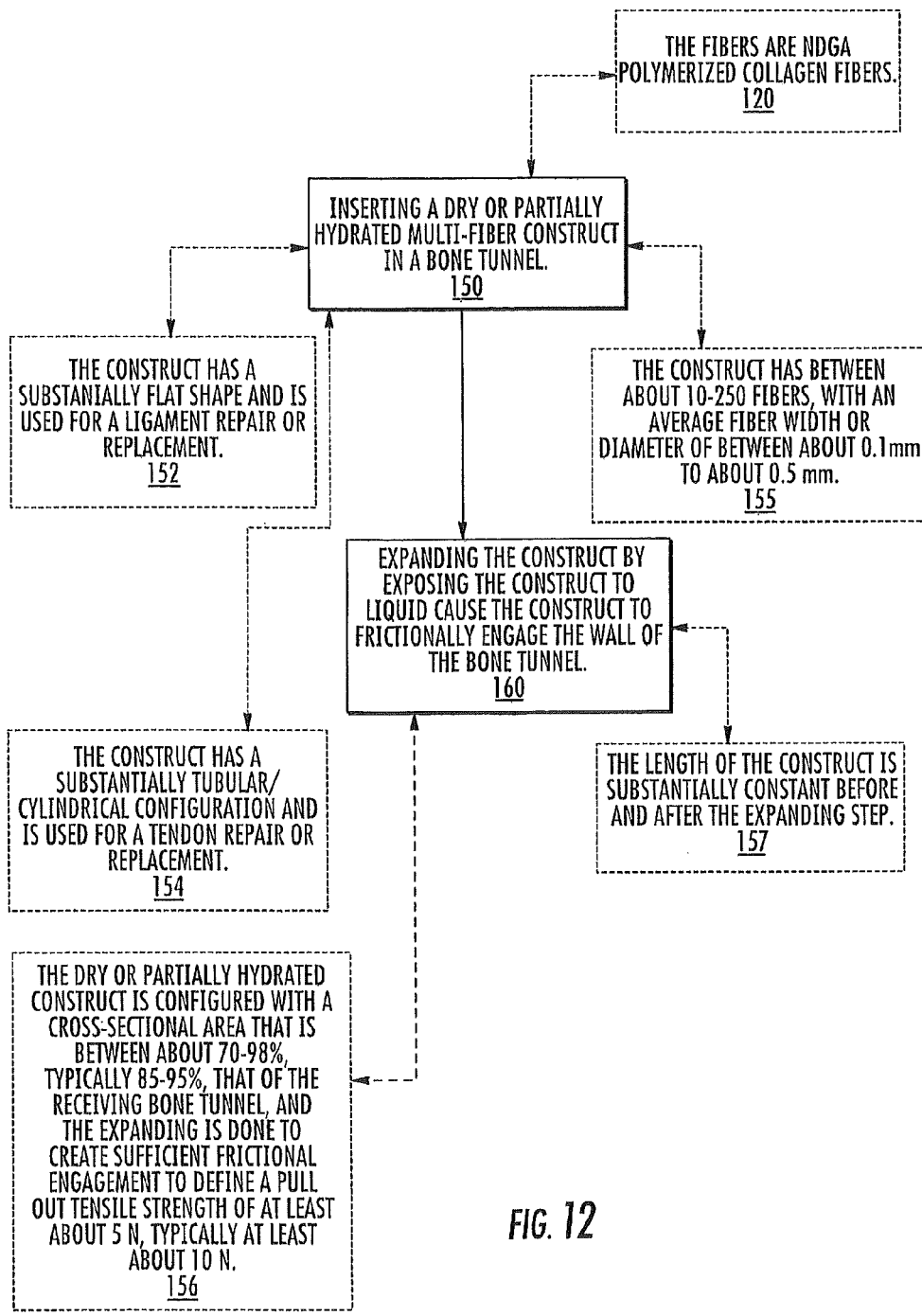
FIG. 12 is a flow chart of operations that can be used to carry out embodiments of the invention.

FIG. 12 illustrates some operations that can be used to carry out embodiments of the invention. As shown, a multi-fiber construct is inserted into a bone tunnel (block 150). The construct is expanded by exposing the construct to liquid to cause the construct to frictionally engage the wall of the bone tunnel (block 160). The dry or partially hydrated construct can be configured with a cross-sectional area that is between about 70-98%, typically 85-95%, of that of the receiving bone tunnel, and the expanding is done to create sufficient frictional engagement to define a pull-out tensile strength of at least about 5 N, typically at least about 10 N (block 156).

The fibers may comprise NDGA polymerized collagen fibers (block 120). The construct can have between about 10-250 fibers, with an average fiber width (diameter) of between about 0.01 mm to about 0.10 mm, typically between about 0.1 and 0.5 mm (block 155). The length of the construct can be substantially constant (during the insertion step and after the expanding step) (block 157). The construct can have a flat shape and may be used for a ligament repair or replacement (block 152). The construct can have a substantially solid core tubular configuration or substantially circular cross-section and can be used for a tendon repair or replacement (block 154).

Optionally, the construct can be implanted in a patient using the hydraulic fixation and one or more of a suture, suture anchor, staple, cap, bone anchor and the like. The suture, where used, can be a suture with an atraumatic needle and may be pre-applied to the construct and packaged in a medical kit for subsequent use.

Also, the construct can optionally include (e.g., be coated, impregnated and/or amalgamated with) a gel or other material. The coating may be to promote fibroblasts, and/or may comprise one or more of an anti-inflammatory agent, an antibiotic or other therapeutic agent.

Figure 13:
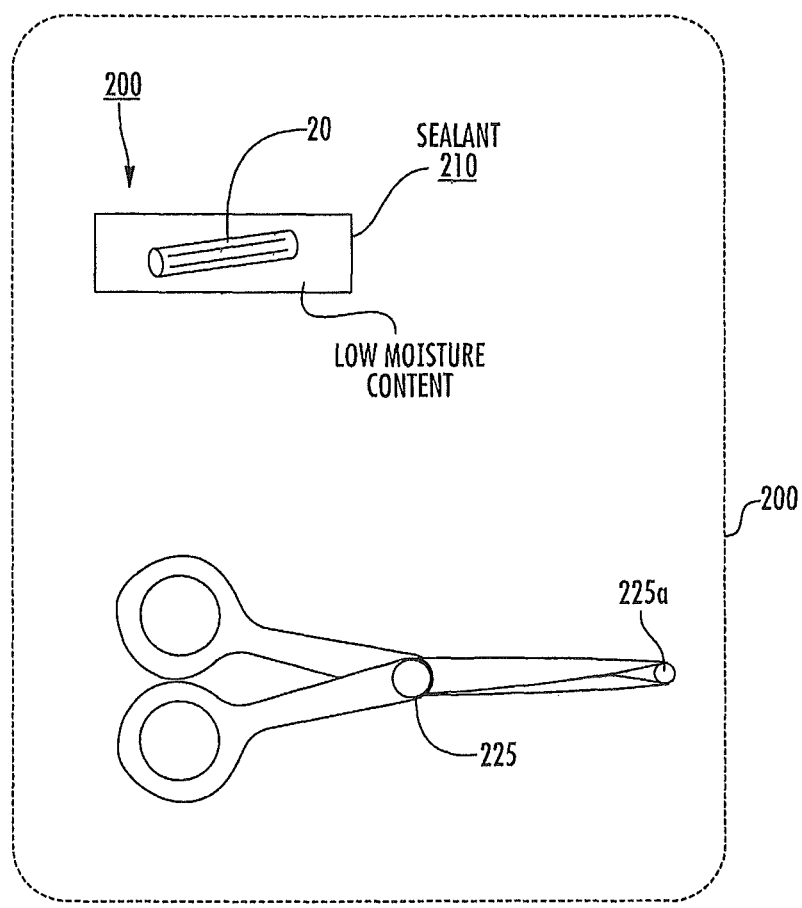
FIG. 13 is a schematic illustration of a medical kit according to embodiments of the present invention.

FIG. 13 is a schematic illustration of a medical kit 200 that includes the hydraulic fixation construct 20. The construct 20 can be held in a sealant 210 that holds the construct in a dry or partially hydrated state. The package 200 may include a desiccant to help maintain the desired dry or partially hydrated state of the construct 20. The sealant 210 may be a flexible, sealed sterile bag that is substantially impermeable at normal atmospheric conditions. The kit 200 may optionally include a modified hemostat tool 225 that includes an axially extending aperture 225a through the centerline of the tool 225 that is sized and configured to snugly hold the leading edge of the construct 20 to slidably insert the construct in position in the bone tunnel 100t.

The construct 20 can be preformed in different lengths for selection by a clinician during a surgical procedure or can be cut to length in situ by a clinician. The construct 20 can be preformed with a suture(s) 105 attached to one end of the construct and provided in the medical kit to reduce on-site preparation time. This latter embodiment may be particularly suitable where the construct 20 is provided in predetermined lengths. The construct 20 can be configured to have a strength and stiffness similar to natural tendon or ligament and can provide an effective scaffold for neo-tendon and ligament to grow into and further enhance some repairs. The kit 200 may include a temperature warning so that the construct 20 is not exposed to unduly hot temperatures that may degrade the implant. A temperature sensor may optionally be included on the package of the kit (not shown) to alert the clinician as to any excessive or undue temperature exposure prior to implantation.

The fibers 10 can be any biologically compatible fibers formed in any suitable manner that can function as a biomedical product (implant/construct). The construct 20 is suitable for chronic implantation and may optionally be absorbed, resorbed and/or biodegradable over time.

In particular embodiments, the fibers can comprise collagen fibers such as glutaraldehyde cross-linked collagen fibers and/or NDGA-treated collagen. Suitable ways of forming NDGA polymerized and/or treated fibers are described in U.S. Pat. Nos. 6,565,960 and 6,821,530, the contents of which are hereby incorporated by reference as if recited in full herein. Generally stated, bulk collagen can be solubilized by digestion with a protease, then extruded into a synthetic fiber. Properly processed NDGA polymerized fibers are biocompatible. After the polymerization process, the fibers can be washed in ethanol and phosphate buffered saline to remove cytotoxins due to leachable reaction products.

Figure 14A:
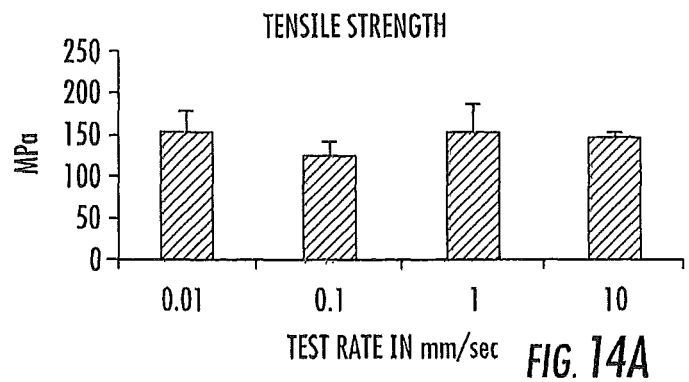
FIG. 14A is a graph of tensile strength of NDGA fibers of different fibers showing strength (MPa) versus test rate in mm/sec.
Figure 14B:
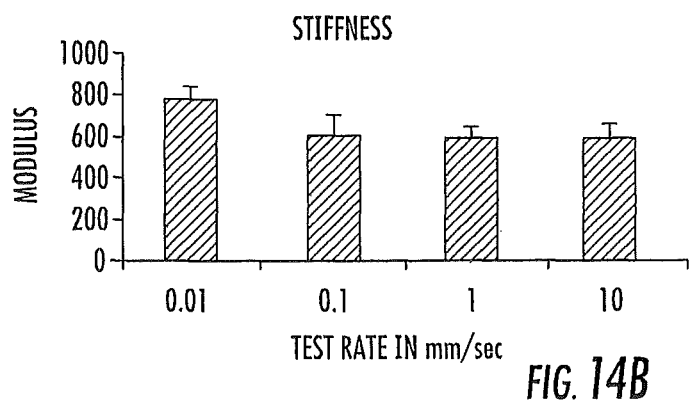
FIG. 14B is a graph of stiffness of NDGA fibers of different fibers showing modulus versus test rate in mm/sec.
Figure 14C:
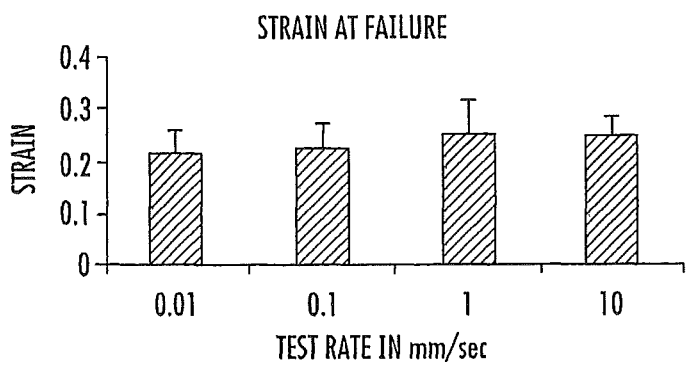
FIG. 14C is a graph of strain at failure of NDGA fibers of different fibers showing strain versus test rate in mm/sec.

NDGA-treated collagen fibers are biocompatible and have desirable mechanical properties. FIGS. 14A-14C illustrate exemplary properties of NDGA-treated collagen fibers of different sizes (0.01, 0.1, 1 and 10 mm). The diameter of the fibers was measured with a dial caliper to the nearest 0.1 mm. The fibers were mounted in clamps with 2 cm nominal tested length. Fibers were deformed to failure. The linear portion of the stress/strain curve was used to calculate the elastic modulus (stiffness) and the force at which the fibers failed was normalized to cross sectional area yielding tensile strength. Values shown are means+/−S.D. for six specimens. For additional discussion of the NDGA polymerized fibers, see, Thomas J. Koob, *Biomimetic approaches to Tendon Repair*, Comparative Biochemistry and Physiology Part A 133 (2002) 1171-1192. See also, co-pending U.S. Provisional Application Ser. No. 60/883,408, Filed Jan. 4, 2007 to Koob et al., entitled, Methods of Making High Strength NDGA Polymerized Collagen Fibers and Related Collagen-Prep Methods, Medical Devices and Constructs, the contents of which are hereby incorporated by reference as if recited in full herein.

The array or bundle 20 can be formed with fibers 10 having widths or diameters in any suitable range, typically in the range of between about 0.01-10 mm. One or more of the fibers 10 may be continuous or discontinuous over the length of the construct 20. Fibers 10 of different widths or diameters may be used in a particular construct 20.

The present invention is explained in greater detail in the following non-limiting Examples.

EXAMPLES

Figure 15:
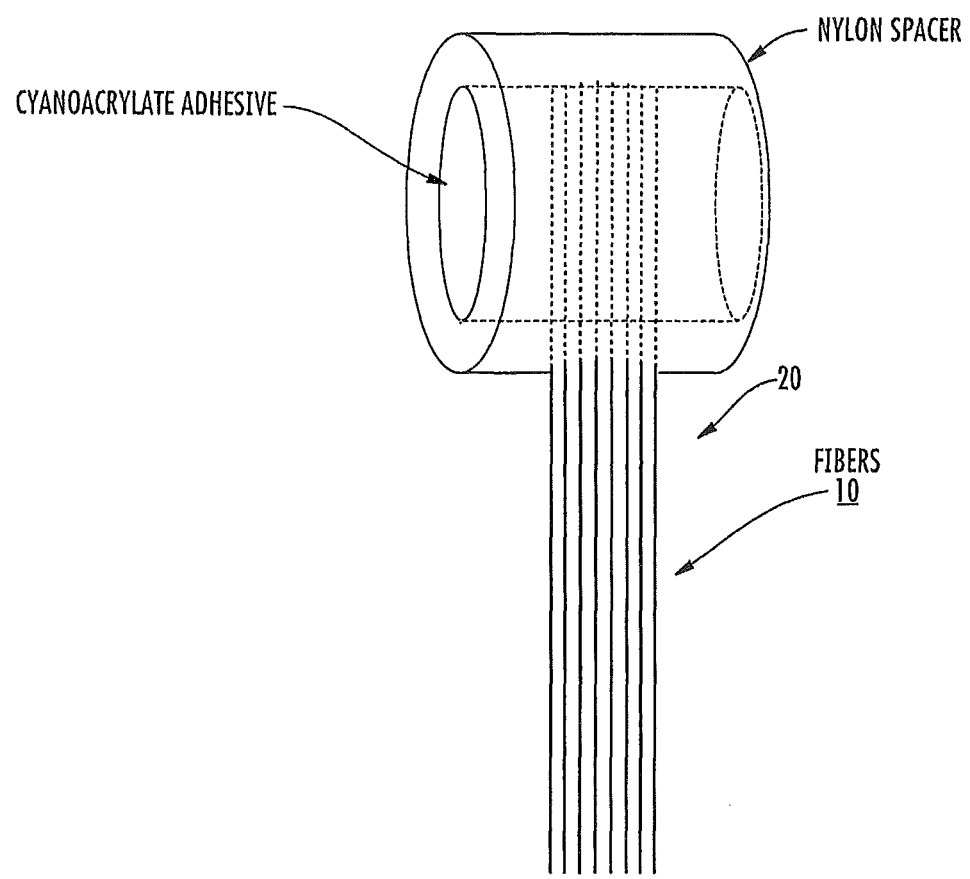
FIG. 15 is a schematic illustration of a construct with biological fibers potted in cyanoacrylate adhesive on the inside of a nylon spacer.

The following discussion describes a study of mechanical properties of hydraulically fixed polymerized collagen fibers in bone tunnels Materials and Methods Biological fibers: NDGA polymerized collagen fibers were prepared substantially as previously described in Koob et al., *Material properties of NDGA-collagen composite fibers: development of biologically based tendon constructs*, Biomaterials, 23:202-212 (2002); and/or as described in co-pending U.S. Provisional Application Ser. No. 60/883,408, titled, Methods of Making High Strength NDGA Polymerized Collagen Fibers and Related Collagen-Prep Methods, Medical Devices and Construct, the contents of the above are incorporated by reference as if recited in full herein. Dried fibers averaged 0.26±0.04 mm in diameter. Hydrated fibers had a mean tensile strength of 90±15 MPa or 10±1N breaking force, Dry fiber constructs were made by arranging fibers in a round parallel array with one end glued (Loctite 454 cyanoacrylate) to round nylon spacers (4.8 OD×2.0 ID×3.2 mm) used for clamping for mechanical testing. The other end of the construct was left intact for insertion into the bone tunnel (FIG. 15). The length of the construct was such that there was a 5 mm unconstrained length (the distance between the bone and the clamped spacer). Ten-fiber constructs were used on all tests except for the scale-up series described later.

Glutaraldehyde crosslinked fibers were prepared by cross-linking collagen fibers overnight in a solution of 2.5% glutaraldehyde in 0.1 M $NaH_2PO_4$, pH 7.0. These collagen fiber constructs were prepared following the procedure described above for the NDGA fibers. After cross-linking, the fibers were washed twice with 70% ethanol for one hour and dried for at least 2 hours under 0.06 N tension to keep them straight.

Bone Tunnels: Bovine metatarsus was obtained fresh from 14 week old calves from a local slaughterhouse. Cortical bone specimens were cut from the mid-shaft using a band saw, and the cancellous specimens were taken from the proximal phalanx of the metatarsalphalangeal joint. Sections were made perpendicular to the long axis. Specimens were brought to final dimensions by polishing on an #220 grit abrasive sheet on a flat surface. Through tunnels were drilled parallel to the long axis of the bone using high-speed steel drill bits (Small Parts Inc., Miami Lakes, Fla., USA). To reduce the effects of frictional heat, the drilling was done on a small milling machine at approximately 70 rpm and 2 mm per minute feed rate (Sherline Model 4000, Sherline Manufacturing Inc, San Marcos, Calif., USA). Phosphate buffered saline (PBS: 0.1 M $NaH_2PO_4$, 0.15 M NaCl, pH 7.0) was used to lubricate the drill bit. The height of the bone corresponded to the insertion depth. During the cutting and polishing, the specimens were irrigated with PBS and were stored for up to 2 hrs at 4° C., pending insertion. For ease of clamping, the bones were further cut into sections not less than 5 mm square in cross section.

Insertion of fiber constructs: A tool to insert the fiber bundles was fabricated by drilling a hole through the centerline of the jaws of a hemostat. The hole size approximated the diameter of the dry fiber bundle. This allowed gripping the fiber bundle into a tight circle for ease of insertion. The fibers were inserted into the bone tunnels until flush with the distal end. The specimens were then submerged in PBS and incubated at 4° C. for 16 hrs. Preliminary experiments determined that this time was sufficient to attain full hydration of the fiber construct.

Swelling: Changes in diameter as a result of hydration to equilibrium were measured on ten fiber constructs by gauging with a template consisting of holes of varying diameters drilled into a 5 mm thick Lexan plate. Hole diameters were verified using a Super Hole Gage, Bacor Inc., Deerfield, Ill., USA. Changes in length were measured with a dial caliper.

Figure 16:
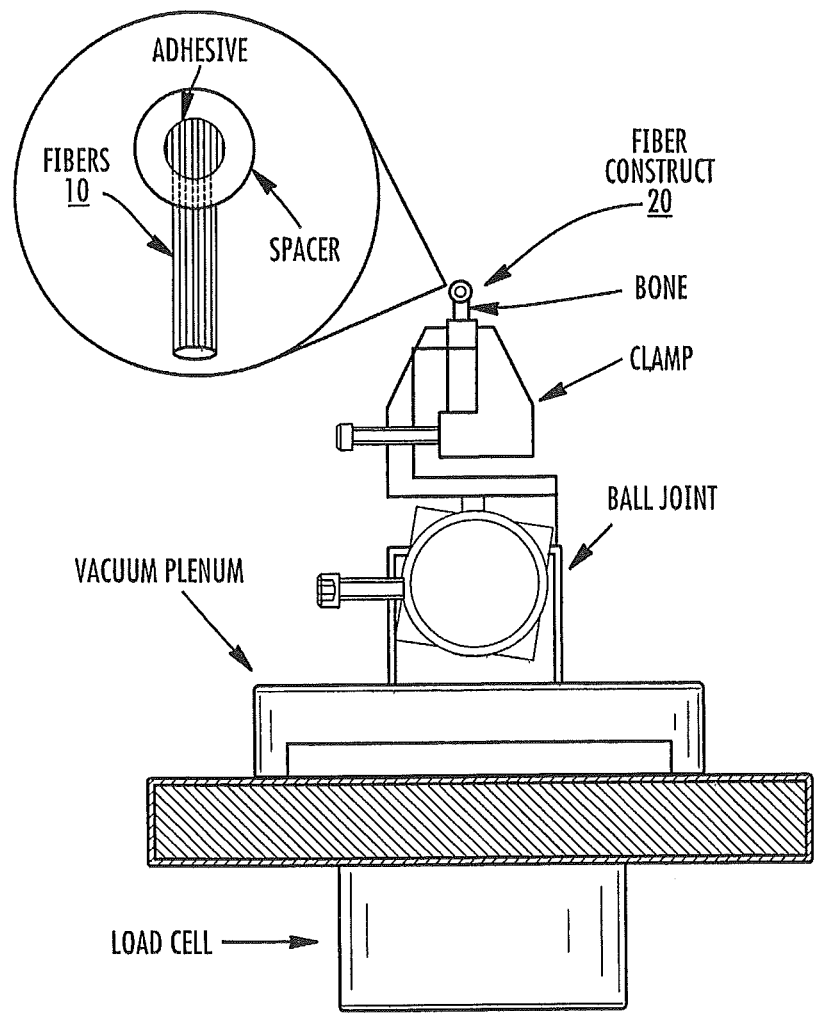
FIG. 16 is a schematic illustration of a text fixture used to mount and orient the construct in-bone in a MTS (Material Testing System).
Figure 17:
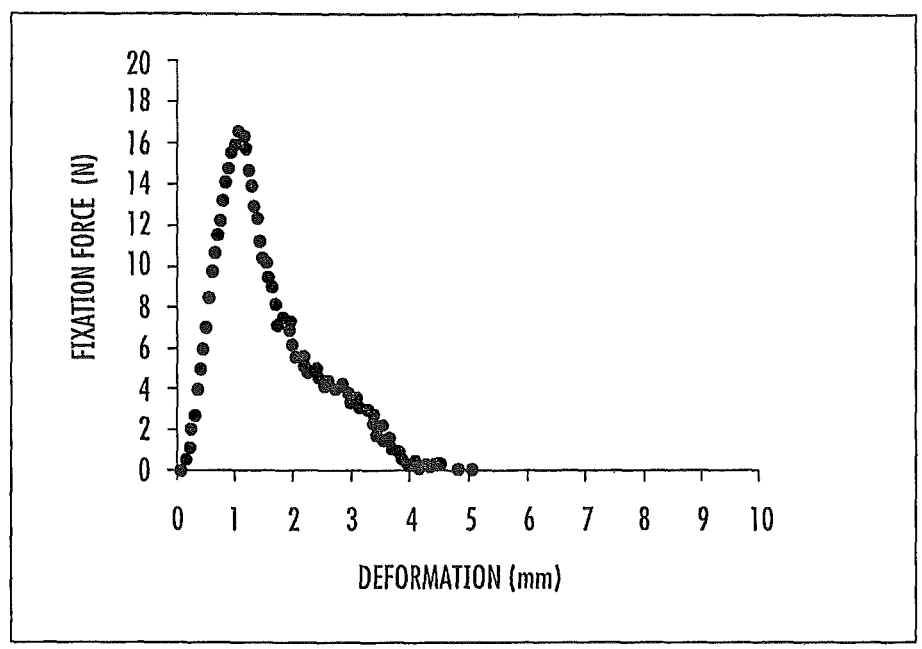
FIG. 17 is a graph of force (N) versus deformation (mm) for a 10-fiber construct hydraulically fixed in a 0.95 mm diameter by 5 mm bone tunnel. Maximum fixation force is interpreted as the peak of the force curve.

Mechanical Tests: The force required to pull out the hydraulically fixed fiber constructs from the bone tunnels was measured with uniaxial tests on an MTS materials testing apparatus (858 Minibionix II, Eden Prairie, Minn., USA). The displacement rate of the piston was set at 1 mm per second. Force and displacement were recorded at 20 Hz. The bone portion of the specimen was clamped to a specially designed ball-jointed device fitted with a vacuum plenum (FIG. 16). This fixture allowed precise parallel alignment of the bone tunnel and construct with the piston transit. The nylon spacer holding the fiber construct was clamped to the piston with standard compression clamps. The pullout force was taken as the peak of the force/deformation curve (FIG. 17). Five replicate specimens were tested for each experimental group.

Effect of tunnel dimensions: To assess sensitivity of varying the prosthesis to tunnel clearance, 10-fiber constructs averaging 0.89±0.01 mm were tested in 5 mm long tunnels with varying bone tunnel diameters (0.95, 1.0, 1.1, 1.2, 1.65 and 2.35 mm). Tunnel depth sensitivity was determined using 0.95 and 1.0 mm diameter tunnels, with depths of 1, 2, 3, 5, 6 and 9 mm in cortical bone and 0.95 mm diameter and depths of 1, 2, 3, 5, 7, 9, and 11 mm in cancellous bone. The additional 11 mm depth in the cancellous bone was chosen to illustrate a plateau in the fixation force progression beyond a critical maximum depth.

Friction Coefficient: Hydrated fibers were wound 10 times around a stainless steel plate measuring 20×20×5 mm and placed on top of a flat section of cortical bone of the same dimensions, which was fixed to a tilt platform (N=5). The platform was slowly tilted until the top plate started sliding. The difference in height of the tilted edges was measured and the angle of repose was obtained with trigonometry. The Measured Friction Coefficient was defined as the tangent of the angle of repose. See, e.g., pp. 3-24, Avallone et al., *Marcs' Standard Handbook for Mechanical Engineers*, (Mc-Graw-Hill Book Co., 1987).

As a comparison, the Calculated Friction Factor was obtained starting with the formula:

$$F_P = F_c F_N \quad \text{(Equation 1)}$$

where $F_p$ is the pull-out or fixation force, $F_c$ is the friction factor and $F_N$ is the normal force produced by the pressure (P). Since, $F_N = AP$ and $A = L\pi D$, where "A" is the area of the tunnel, "D" is the internal diameter and "L" is the depth. Combining equations and rearranging yields:

$$F_c = F_P/(PL\pi D) \quad \text{Equation (2)}$$

Equation (2) was used to obtain the Calculated Friction Coefficient.

Pressure: In order to approximate the swelling pressure generated by the fibers as they hydrate in a confined space, the change in dimensions of Polytetrafluorethylene (PTFE) tubing (Small Parts Inc., Miami Lakes, Fla., USA) vs. the pressure generated by hydraulically loading the tubing was measured. The inner diameter of the tubing was 0.95 mm, matching the optimal bone tunnel diameter as established in FIGS. 19A and 19B. The wall thickness was 0.15 mm. Bundles of 10 parallel dry fibers were placed inside the PTFE tubing. The fiber-in-tubing units were placed in PBS and allowed to hydrate for 16 hrs. The changes in outside diameter resulting from the internal pressure exerted by the fibers were measured with a micrometer. An identical section of tubing was connected to a 3 ml syringe filled with water that was progressively compressed by the MTS machine, thereby subjecting the tubing to progressively higher pressure. The outside diameter of the tubing was measured at sequential pressure points. The pressure was calculated by dividing the force measured by the load cell of the MTS machine by the internal cross sectional area of the syringe. This method neglects the internal deformation of the tubing thickness; therefore, the results represent the minimum pressure generated by the fibers in a rigid tunnel. This effect was not expected to be significant.

Fill percentage of the dry construct in the bone tunnel was calculated by taking the total cross sectional area of the dry fibers and dividing by the cross sectional area of the bone tunnel. The largest and smallest diameter of each fiber was measured with a dial caliper and the formula for the area of an ellipse was used to calculate the area. The calculated pressure was defined as the fixation force divided by the product of the internal surface area of the tunnel area and measured friction factor, $P=F_p/(F_F A)$.

Scale up: To assess the potential for scaling up to different sized constructs, 6, 10, 13, 16, 32, and 48 fiber constructs were tested. The tunnel diameters were designed to follow a linear progression of the aggregate areas of the bundles using the 10 fiber construct as the basis. This yielded tunnel diameters of 0.76, 0.95, 1.07, 1.16, 1.65, and 2.35 mm, respectively, which included adjustments within a 3% margin to allow for the use of commercially available drill bits.

Statistical Analysis—The student T-Test was used to determine statistical significance (p<0.05). N=5 on all tests.

Results

Fiber Swelling

As the 10-fiber constructs swelled from their dry state to a state of unconstrained hydrated equilibrium, they increased an average of 45.8±3.0% in diameter and 213±8.8% in cross sectional area. Changes in length were negligible (<1%) therefore the volume change was also 213±8.8%

Effects of Tunnel Depth

Figure 18A:
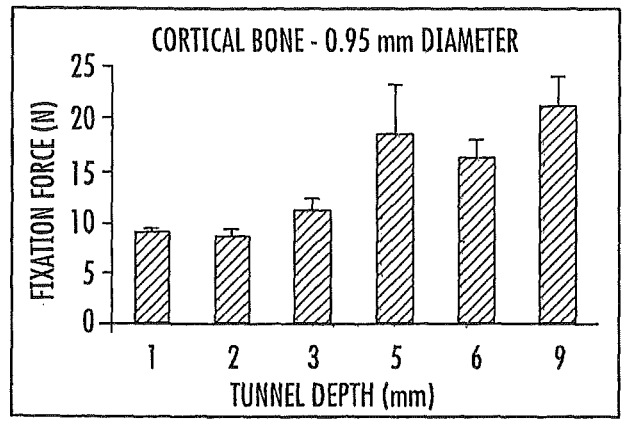
FIGS. 18A-18C are graphs of fixation force (N) versus tunnel depth (mm) for constructs made of 10-fiber NDGA cross-linked fibers (the number of samples "n" is 5 for each bar and error bars in the graph show the standard deviation).
Figure 18B:
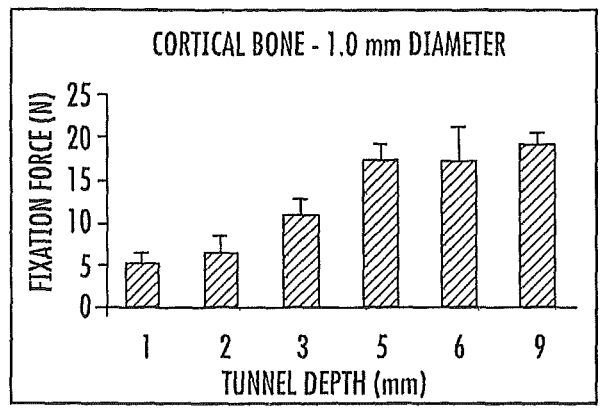
Figure 18C:
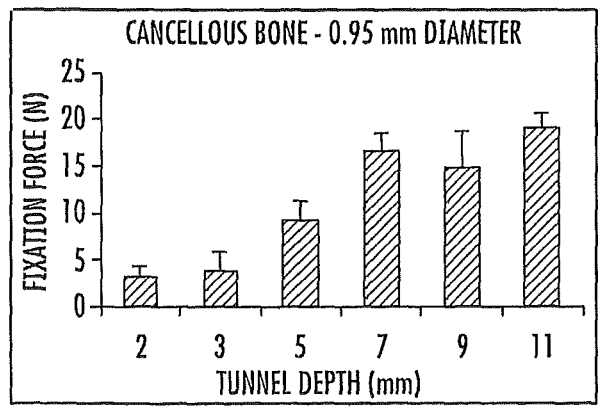

Pullout tests of the constructs inserted into bone with a 5 mm unconstrained fiber length produced smooth force/displacement curves (FIG. 17). The force increased sharply with small piston displacement as expected with an effective fixation. Bone tunnel depth directly influenced fixation strength. In cortical bone, the fibers showed a trend of increasing fixation strength with increasing length of insertion for a 0.95 mm diameter bone tunnel (FIG. 18A). For a tunnel diameter of 1.0 mm, the force of pull-out followed a similar trend but with slightly lower forces in the shorter tunnels (FIG. 18B). Both curves reached an apparent maximum plateau at 5 mm tunnel length. The force at 5, 6, and 9 mm lengths averaged 18.7±3.9 and 17.6±2.0 N for the 0.95 and 1.0 mm diameters, respectively. At 5 mm depth, 3 of 5 of the specimens broke at the bone or spacer interface; at 7 and 9 mm all of the specimens broke rather than pulled out. The fiber bundle inserted into cancellous bone tunnels showed a similar trend to that of fibers in cortical bone, but the plateau was reached at 7 mm and the average pullout force for 7, 9, and 11 mm was 16.8±3.1 N (FIG. 18C). At 5, 7 and 9 mm insertion depths the fibers pulled out of the bone tunnel; at 11 mm depth, all the fiber constructs broke before pullout.

Effects of Tunnel Diameter

Figure 19A:
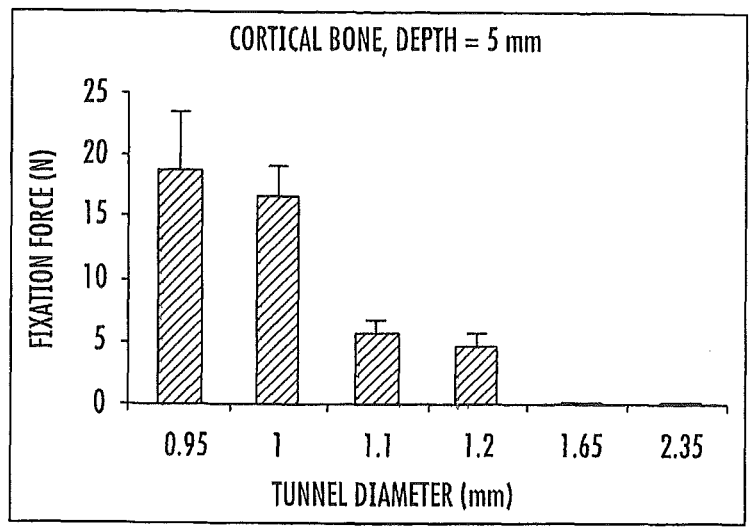
FIGS. 19A and 19B are graphs of fixation force (N) versus tunnel diameter (mm) for 10-fiber constructs (the number of samples "n" is 5 for each bar and error bars in the graph show the standard deviation). Diameters were varied while the depth was constant at 5 mm for cortical bone (FIG. 19A) and 7 mm for cancellous bone (FIG. 19B).
Figure 19B:
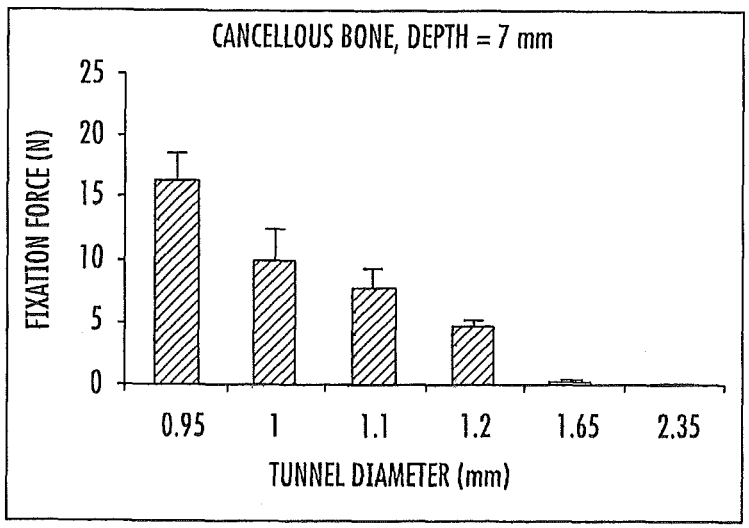

The effect of bone tunnel diameter on fixation strength was examined using the 10-fiber constructs and optimal tunnel depths established above (5 mm for cortical bone; 7 mm for cancellous bone). The fixation strength of the constructs showed significant sensitivity to tunnel diameter (FIGS. 19A and 19B). The pullout force decreased as the diameter increased until it reached zero at 1.65 mm diameter for cortical bone (FIG. 19A) and 0.6±0.16 N for cancellous bone (FIG. 19B). At 1.1 mm diameter the average pullout force was 30.3% of that at 0.95 mm diameter for cortical bone and for cancellous bone it reduced to 45.3% for the same diameters.

Pressure and Friction

Figure 20A:
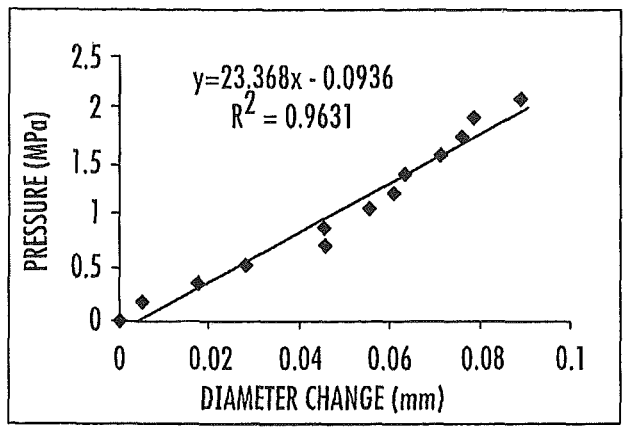
FIG. 20A is a graph of estimated swelling pressure (MPa) of NDGA fibers calculated from pressures associated with a change in diameter of PTFE tubing versus change in diameter (mm).

Plotting pressure vs. change in tubing dimensions yielded a linear regression with $r^2=0.96$ (FIG. 20A). A 10-fiber construct was then loaded into the same tubing and allowed to swell to equilibrium; the change in diameter was measured. Inserting the value obtained into the regression equation yielded an approximate swelling pressure of 1.05 MPa. Inserting this pressure into the friction factor equation described in the methods yielded a Calculated Friction Factor of 1.16±0.35. Fiber to bone friction measured by the angle of repose method averaged 0.907±0.056. The measured friction factor was used in calculations below for the hydraulic pressure exerted on the wall of the tunnel.

Pullout Force vs. Percent Fill

Figure 20B:
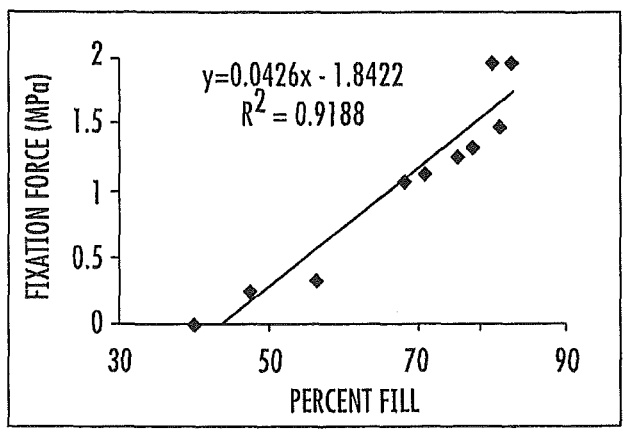
FIG. 20B is a graph of fixation force/cross-sectional area of hole in MPa as a function of percentage fill.
Figure 20C:
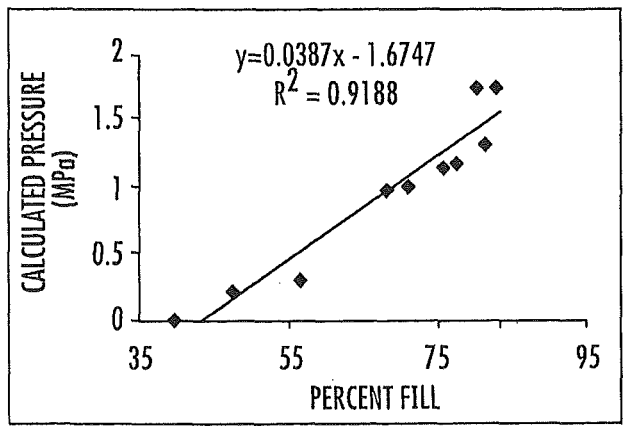
FIG. 20C is a graph of calculated pressure versus percent fill.

The pull-out force was directly related to the percent of the tunnel cross-sectional area filled by the dried fiber construct (expressed as % fill). The greatest fixation was achieved at a % fill greater than 85% (FIG. 20B). This relationship correlated with the calculated pressure vs. % fill (FIG. 20C), indicating that the magnitude of the pull-out force depended on the swelling pressure exerted on the bone tunnel by the fibers in the construct causing a corresponding amount of friction.

Scale-up to Larger Bundles

Figure 21A:
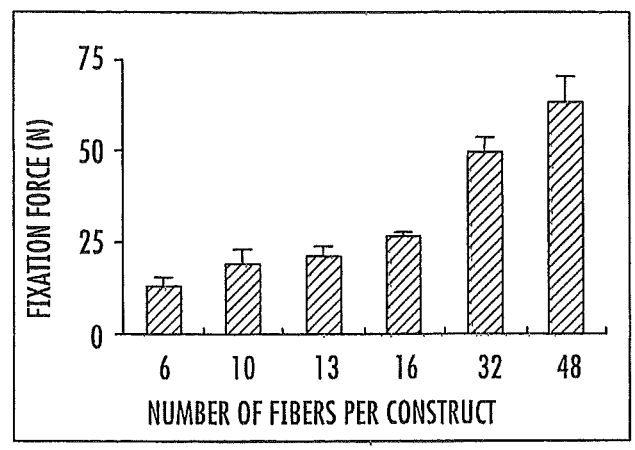
FIG. 21A is a graph of fixation force (N) versus a number of fibers in the construct using a 5 mm long tunnel with the tunnel diameters designed to provide a constant fit with the construct diameters (sample size n=5, error bars show the standard deviation).
Figure 21B:
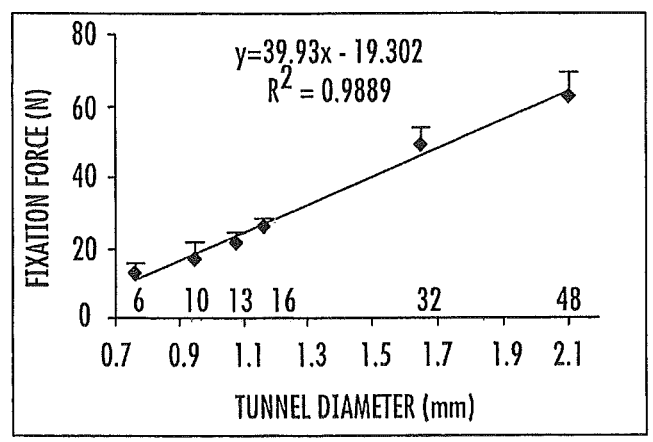
FIG. 21B is a graph of fixation force (N) versus tunnel diameter (mm). The number of fibers in the construct at each diameter is shown by the numbers directly above the x-axis.

At constant tunnel depth, fixation strength scaled up as a linear function of the diameter of the tunnel and, therefore, of the diameter of the fiber bundle (FIGS. 21A and 21B). For the 48 fiber constructs in a 2.10 mm diameter tunnel, the fixation strength averaged 63.3±6.9 N.

Glutaraldehyde Cross-linked Fibers

Figure 22:
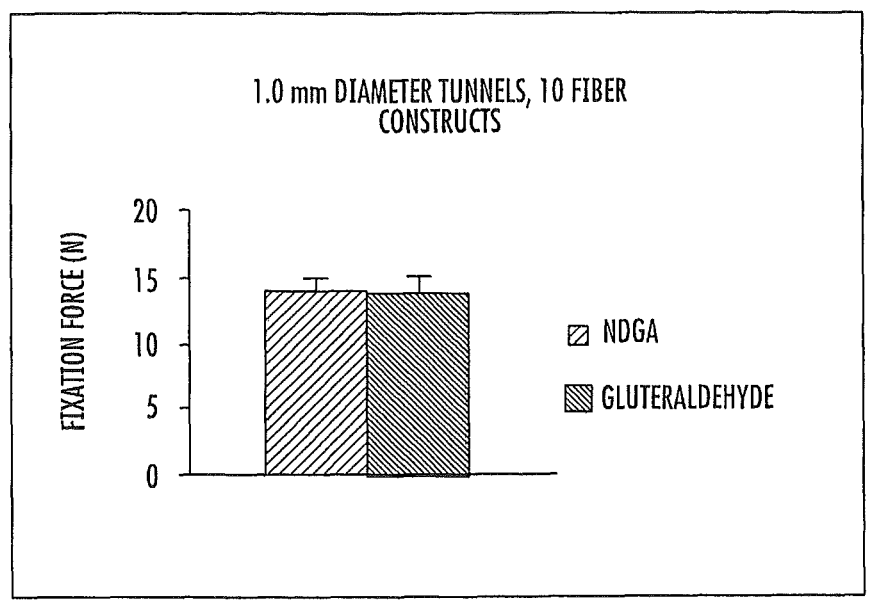
FIG. 22 is a graph of fixation force (N) of two different biological fibers, NDGA and glutaraldehyde cross-linked fibers, both used to form 10-fiber constructs. Both were hydrated overnight in saline to cause the hydraulic fixation. Tunnel diameters were 1.0 mm, tunnel depths were 5 mm, n=5, and the error bars in the graph show the standard deviation.

Constructs made with glutaraldehyde cross-linked fibers showed similar hydraulic locking forces to those of NDGA cross-linked fiber constructs (FIG. 22).

Discussion

Embodiments of the present invention can provide a novel and effective strategy for joining biologically-based fibrous materials to bone tunnels. Hydraulic fixation may serve as an adjunct fixation strategy or optimally eliminate the need for mechanical fixation devices.

The basis for hydraulic fixation is swelling of the fibers as they imbibe liquid (water) and cause an increase in pressure inside the bone tunnel. The pressure acts along the internal surface area of the tunnel and produces a "locking force" as a result of friction. One simple model of friction force applied to this situation describes the friction or fixation force as equal to the normal force times the friction factor, $F_P = F_N F_F$. The normal force equals the pressure times the internal surface area of the bone tunnel, $F_N = PA$. The above model is validated by the correlation of Measured Friction Coefficient between bone and fibers with the Calculated Friction Coefficient. This correlation also suggests that the effect of any deformation of the interior of the PTFE tubing used to measure swelling pressure had a minimal impact on the results. Since $A = \pi DL$, where D is the diameter and L is the depth of the bone tunnel, the above equations can be combined to yield $F_P = P\pi DLF_F$. Therefore, $F_P$ (fixation force) should increase linearly as either the diameter (D) or the depth (L) of the bone tunnel are increased, as long as a substantially constant fit (percent fill) between the construct and tunnel is maintained. Increasing the construct size while maintaining a constant fit and depth produced a linear relationship as predicted above (FIGS. 21A, 21B). While it may be postulated that load sharing with larger constructs between the fibers might be an issue, this was not evidenced since the results of the scale-up were linear as predicted. This might be accounted for by fiber-to-fiber engagement, e.g., frictional engagement, since the internal fibers were likely subjected to a similar pressure of those in contact with the bone tunnel wall.

Varying the diameter of the tunnel while maintaining a constant construct size showed that the highest fixation force and presumably the highest pressure resulted from the tightest initial fit between the construct and tunnel. Pull-out strength deteriorated rapidly as the tunnel diameter to construct fit was made looser. There was a linear relationship between calculated pressure and percent fill, further supporting the likelihood of a correlation of fill or tunnel size to initial prosthesis size (and/or swelling).

Assuming constant pressure and friction factor, the total fixation force can be represented as the sum of the forces at each plane and can be modeled by integrating force over the length of the insertion using the equation:

$$F = \int_0^l P\pi D dx. \quad \text{Equation (3)}$$

Bringing out the constants and integrating yields:

$$F = P\pi Dl \quad \text{Equation (4)}$$

where F is the cumulative force at the depth l. This equation describes a linear progression of accumulated force starting at zero at depth l to a maximum equal to the pull force F at the surface of the bone facing the source of tension. Seen another way, force will act upon the fibers to a layer deep enough to generate the required total fixation force. The force required for pullout or breaking of the construct limits the total force generated. For deep enough insertions the construct will break rather than pull out (FIGS. 18A-18C). This was evident in cortical bone tunnels measuring 5 mm or more in depth. For forces less than those required for breaking or pull-out, the fibers should be stressed up to the depth necessary to withstand the applied force. At levels deeper than those required to generate the necessary force to resist pull-out there should be no force acting on the fibers, and no deformation or movement should occur in the deeper levels of the fibers.

For constructs of 10 fibers in tunnels of 0.95 mm diameter, the integration by hydraulic fixation of NDGA-crosslinked fiber constructs in bone is stronger than the construct itself at tunnel depths exceeding 5 mm in cortical bone and 7 mm or longer in cancellous bone. The integration of biological fibers into a bone tunnel via hydraulic fixation could be useful for some repairs of avulsed tendons and torn ligaments where the desired fixation forces are within the capabilities of this method. In some applications, hydraulic fixation may not require the use of peripheral devices such as bone anchors, screws, buttons, sutures, glues or resins. In some embodiments, the techniques described herein may advantageously not add additional materials to the surgical placement and anchoring of a fibrous bioprosthesis, thereby reducing or eliminating the need for harvesting autografts. Additionally, maximum fixation force may be obtained within hours of insertion, allowing early mobilization and resultant therapeutic advantages.

Potential applications include the development of prostheses for tendon transfers, repair of tendon avulsions and supplementing anterior cruciate ligament (ACL) repairs. Pediatric applications are especially attractive since it may allow for relatively short bone tunnels that would avoid interfering with the growth plates. The number of fibers, aggregate diameter and tunnel depth can be designed taking into consideration the strength of the fibers and the required strength of the application, which can be a function of the strength of normal tendons and ligaments, anatomical site, and patient size and age. The design of the tunnel diameter should be considered since the integration can, in some embodiments, be sensitive to the fit between the construct and the tunnel. It is contemplated that hydraulic fixation of fiber constructs potentially operates effectively at larger construct sizes than those tested and therefore can be designed to fit various applications, and is not limited to those described herein.

It is contemplated that the rate of hydration in the bone tunnel may be controlled for some applications to allow sufficient time for surgical placement of a bioprosthesis and, if needed, adjustment of length and tension. The amount of time after the fibers are exposed to a hydrating environment and the speed of fixation can be coordinated so as to avoid premature locking. A means of fast insertion and/or controlling the rate of hydraulic swelling in vivo may be used, for example, hydrogel matrices are potential hydration retardants.

Another advantage of the swelling properties of the fiber constructs is that swelling occurs substantially only perpendicular to the long axis of the fiber. The constructs do not substantially lengthen or shorten. Applying the proper tension in the re-attachment of tendons or ligaments to bone would not suffer from problematic lengthening of the construct due to hydration.

While these data establish that hydraulic fixation results in mechanical coupling of biological fibers to bone, other factors may influence the ultimate performance of a fibrous bioprosthesis. The objective of using such a bioprosthesis to connect tendons or ligaments to bone is to provide immediate and sufficient stabilization to allow early rehabilitative mobilization. However, the ultimate fixation strength will rely on the mechanobiology of the bone. The best outcome would be complete osteointegration of the fiber construct without producing untoward stress concentration at the fiber-bone interface.

NDGA polymerized collagen fibers may be particularly suitable for implementing the hydraulic fixation. They can provide the swelling properties for effective hydraulic fixation, they are not cytotoxic, they do not harbor diffusible cytotoxic reaction products, they are biocompatible with cells in vitro, and they are biocompatible and can be configured so that they do not get degraded for six weeks in vivo. See, Koob, *Biomimetic approaches to tendon repair*, Comp. Biochem. Physiol. A Mol. Integr. Phys. 133: 1171-1192 (2002). The biocompatiblility of these fibers combined with biomechanics similar to natural tendon and ligament offer a potential of serving as effective scaffolding for new tissue growth. In a functional context, the optimal mechanical performance of hydraulic fixation is only as good as the tensile properties of the anchored bioprosthesis. This was the case in the scale-up experiment in which the 6-, 10-, 13- and 16-fiber prostheses broke before pulling out of the tunnel. NDGA-polymerized fibers used in this study exhibit material properties in uniaxial tensile tests that are comparable to those of tendons and ligaments. However, when bundled in linear arrays and hydraulically fixed in bone, stress concentration at the prosthesis bone junction apparently lowers the aggregate tensile strength of the bioprosthesis. For example, the 10-fiber prosthesis failed at 18.6 N, in contrast to the theoretical tensile strength of 100 N. Despite this lowered force at failure, the stress at the failure site, calculated by dividing the force by the cross sectional area of the tunnel, averages 24.4+/−3.6 MPa. The tensile strength of tendons ranges from 40 to 100 MPa. Although this performance is lower than that of natural tissue it could be enough to maintain the integrity of the repair until neo-tendon and neo-ligament growth augments the total strength of the repair.

One potential application is the repair of digital flexor tendons, where the median forces of active and passive mobilization were found to be 27 N. Flexion. Flexion under a 500 g load produced a median force of 48 N. See, Trail et al., *Forces transmitted along human flexor tendons during passive and active movements of the fingers*, J. Hand Surg., 29:4:386-389 (2004). As tested, constructs of 48 NDGA polymerized collagen fibers in a bone tunnel of 2.1 mm diameter and 5 mm depth withstood an average force of 63.3±6.87 N. A prosthesis of similar size and fixation strength could be developed for flexor tendon repair that could allow early passive and active motion and light initial use.

In conclusion, hydraulic fixation can provide a simple and effective means for joining biological fibers to bone either alone or in conjunction with another fixation device. Bioprosthesis could be developed using a parallel array of NDGA polymerized fibers that relies on hydraulic fixation as the coupling modality in bone. NDGA-crosslinked fibers are mechanically competent as compared to native tendons and ligaments and they have excellent biocompatibility. Such a medical device could provide the surgeon the advantages of simple and effective placement, adjustment and fixation. The device could deliver cytokines for enhanced osteointegration. Additionally, hydraulic fixation may allow passive motion within hours of surgery and could potentially be used in a variety of applications such as, for example, digital flexor tendon repair. In addition to being strongly fixed within hours it could allow for osteointegration of the fibers into the regenerated bone tissue and serve as a scaffold for neo tendon and neo ligament growth and a corresponding augmentation of strength and reliability.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A medical rivet, comprising:
an implantable partially hydrated or dry rivet having a length and comprising a plurality of polymerized collagen fibers configured to expand when exposed to liquid to frictionally engage a target local structure to hydraulically affix the rivet in the target local structure,
wherein the polymerized collagen fibers are configured as an array of discrete polymerized collagen fibers,
wherein the discrete polymerized collagen fibers are substantially parallel over at least a major portion of the length of the rivet,
wherein the partially hydrated or dry rivet is flexible,
wherein the partially hydrated or dry rivet has a cross-sectional area that is between about 85% to about 95% that of the target local structure before implantation, and
wherein after no more than 24 hours after implantation, the rivet is configured to swell to a sufficient degree to frictionally engage the target local structure to withstand a pull out force that is at least 15 N.

2. A medical rivet according to claim 1, wherein the rivet is sized and configured to be slidably inserted into two aligned adjacent bone tunnels, then expand to frictionally engage respective walls thereof whereby bones housing the respective bone tunnels are held in alignment.

3. A medical rivet according to claim 1, wherein the plurality of polymerized collagen fibers comprises at least 100 NDGA polymerized substantially parallel collagen fibers defining a substantially cylindrical body.

4. A medical rivet according to claim 1, wherein the rivet is sized and configured for pediatric fracture repairs to extend through bone tunnels in bone plates.

* * * * *